US010330657B2

(12) United States Patent
Greathouse et al.

(10) Patent No.: US 10,330,657 B2
(45) Date of Patent: Jun. 25, 2019

(54) ESTIMATION OF CONDUCTIVITY FOR NANOPOROUS MATERIALS

(71) Applicants: Jeffery Greathouse, Albuquerque, NM (US); Joanne Fredrich, Houston, TX (US); Gary Jerauld, Houston, TX (US); Randall Cygan, Albuquerque, NM (US)

(72) Inventors: Jeffery Greathouse, Albuquerque, NM (US); Joanne Fredrich, Houston, TX (US); Gary Jerauld, Houston, TX (US); Randall Cygan, Albuquerque, NM (US)

(73) Assignee: BP Corporation North America Inc., Houston, TX (US)

( * ) Notice: Subject to any disclaimer, the term of this patent is extended or adjusted under 35 U.S.C. 154(b) by 1211 days.

(21) Appl. No.: 14/566,520

(22) Filed: Dec. 10, 2014

(65) Prior Publication Data

US 2016/0169854 A1 Jun. 16, 2016

(51) Int. Cl.
*G01N 27/04* (2006.01)
*G01N 33/24* (2006.01)
*G16C 20/30* (2019.01)

(52) U.S. Cl.
CPC ............ *G01N 33/24* (2013.01); *G01N 27/041* (2013.01); *G16C 20/30* (2019.02)

(58) Field of Classification Search
CPC ............ H01M 2004/021; G01N 33/24; G01N 27/041; G06F 19/704
USPC .......................................................... 702/27
See application file for complete search history.

(56) References Cited

U.S. PATENT DOCUMENTS

| | | | |
|---|---|---|---|
| 2005/0014905 A1* | 1/2005 | Chung | B82Y 30/00 525/333.7 |
| 2007/0259433 A1* | 11/2007 | Jones | G01N 33/241 436/31 |
| 2012/0172648 A1* | 7/2012 | Seebauer | B82Y 30/00 585/733 |

(Continued)

OTHER PUBLICATIONS

Cygan et al., "Molecular Models of Hydroxide, Oxyhidroxide, and Clay Phases and the Development of a General Force Field", J. Phys. Chem. B, vol. 108 (2004), pp. 1255-1266.

(Continued)

*Primary Examiner* — John E Breene
*Assistant Examiner* — Jeffrey P Aiello
(74) *Attorney, Agent, or Firm* — John Wood

(57) ABSTRACT

Methods and systems for estimating conductivity of clay mineral systems, and for applying the estimates in larger-scale analysis. Conductivity of the clay may be estimated by constructing a molecular model of an anhydrous charge-neutral clay, and then assigning a charge density by substitution of ions in the model of the clay structure. Counterions are inserted for charge neutrality, and water molecules are added to the model to reflect a selected level of hydration. Following assignment of force-field coefficients, molecular dynamics simulation provides data from which diffusion coefficients can be estimated. Application of the Nernst-Einstein relationship to the diffusion coefficients of the counterions provides the ion conductivity of the clay system. This conductivity can be used to derive a formation factor, and can be applied in direct numerical simulation analysis.

22 Claims, 11 Drawing Sheets

(56) References Cited

U.S. PATENT DOCUMENTS

| | | | | |
|---|---|---|---|---|
| 2014/0190876 A1* | 7/2014 | Meyer | ............ | A61M 1/284 |
| | | | | 210/87 |
| 2014/0270394 A1* | 9/2014 | Fredrich | ............ | G06K 9/64 |
| | | | | 382/109 |
| 2014/0311967 A1* | 10/2014 | Grossman | ............ | C01B 32/184 |
| | | | | 210/500.21 |
| 2017/0260068 A1* | 9/2017 | Tappen | ............ | C02F 1/4691 |
| 2017/0312415 A1* | 11/2017 | Pudil | ............ | A61M 1/1696 |

OTHER PUBLICATIONS

Plimpton et al., "Particle-mesh Ewald and rRESPA for parallel molecular dynamics simulations", Proceedings of the Eighth SIAM Conference on Parallel Processing for Scientific Computing (1997).

Bockris et al., Modern Electrochemistry 1: Ionics, 2nd ed. (Plenum Press, New York, 1998), pp. 456-458.

Saarenketo, "Electrical Properties of Water in Clay and Silty Soils", J.App. Geophys., vol. 40, No. 1 (1998), pp. 73-88.

Videla et al., "Aqueous electrolytes confined within functionalized silica nanopores", J. Chem. Phys, vol. 135, Paper No. 104503 (2011).

Yang et al., "Electric Conductivity in Electrolyte Solution under External Electromagnetic Field by Nonequilibrium Molecular Dynamics Simulation", J. Phys. Chem. B, vol. 114 (2010), pp. 8449-8452.

Krienke et al., "Hydration of Molecular Ions: A Molecular Dynamics Study with a SPC/E Water Model", J. Phys. Chem C, vol. 111 (2007), pp. 15935-15941.

Lorenz et al., "Molecular Dynamics of Ionic Transport and Electrokinetic Effects in Realistic Silica Channels", J. Phys. Chem. C, vol. 112 (2008), pp. 10222-10232.

Sala et al., "Specific ion effects in aqueous eletrolyte solutions confined within graphene sheets at the nanometric scale", Phys. Chem. Chem. Phys., vol. 14 (2012), pp. 10799-10808.

Devarajan et al., "Pore-Scale Analysis of the Waxman-Smits Shaly Sand Conductivity Model", SPWLA 47th Annual Logging Symposium (2006), pp. 1-9.

Greenwell H. C. et al: "On the application of computer simulation techniques to anionic and cationic clays: A materials chemistry perspective", Journal of Materials Chemistry, vol. 16, No. 8, Oct. 14, 2005, pp. 708-723.

Boulet P. et al: "Recent advances in understanding the structure and reactivity of clays using electronic structure calculations", Journal of Molecular Structure (Theochem), Eelsevier Science Publishers B.B., Amsterdam, NL, vol. 762, No. 1-3, Apr. 2, 2006, pp. 33-48.

Okamoto M. et al: "Dispersed structure and ionic conductivity of smectic clay/polymer nanocomposites", Polymer, Elsevier Science Publishers B.V., GB, vol. 42, No. 6, Mar. 1, 2001, pp. 2685-2688.

Chou Chang F-R. et al: "Monte Carlo and Molecular Dynamics Simulations of Electrical Double-Layer Structure in Potassium-Montmorillonite Hydrates", Langmuir, vol. 14, No. 5, Feb. 10, 1998, pp. 1201-1207.

Clerouin J. et al: "Electrical conductivity and equation-of-state stud of warm dense copper: Measurements and quantum molecular dynamics calculations", Physical Review. B, Condensed Matter and Materials Physics, vol. 71, No. 6, Feb. 1, 2005.

Arns C.H. et al: "Accurate estimation of transport properties from microtomographic images", Geophysical Research Letters, vol. 28, No. 1, Sep. 1, 2001, pp. 3361-3364.

Arns J-Y. et al: "Relative permeability from tomographic images; effect of correlated heterogeneity", Journal of Petroleum Science and Engineering, vol. 39, No. 3-4, Sep. 1, 2003, pp. 247-259.

Keller T. et al: "An interdisciplinary approach towards improved understanding of soil deformation during compaction", Soil and Tillage Research, Elsevier, Amsterdam, NL, vol. 128, Dec. 7, 2012, pp. 61-80.

Churakov S. V. et al: "Up-Scaling of Molecular Diffusion Coefficients in Clays: A Two-Step Approach", Journal of Physical Chemistry C, vol. 115, No. 14, Mar. 10, 2011, pp. 6703-6714.

Revil A. et al: "Constitutive equations for ionic transport in porous shales", Journal of Geophysical Research American Geophys. Union USA, vol. 109, No. B3, Mar. 10, 2004, p. 19.

Hort R.D. et al: "Analysis of sources of bulk conductivity change in saturated silica sand after unbuffered TCE oxidation by permanganate", Contaminant Hydrology, Elsevier, Amsterdam, NL, vol. 165, Jul. 15, 2014, pp. 11-23.

Sen P. N. et al: "Formation factor of carbonate rocks with microporosity: model calculations", Journal of Petroleum Science and Engineering, vol. 17, No. 3-4, May 1, 1997, pp. 345-352.

Dufey J. E. et al: "Selfdiffusion of anions in clay gels", Analytical Sciences, The Japan Society for Analytical Chemistry, US, vol. 51, No. 2, May 1, 1975, pp. 278-282.

Benning J. L. et al: "The effects of scale and spatial heterogeneities on diffusion in volcanic breccias and basalts: Amchitka Island, Alaska", Contaminant Hydrology, Elsevier, Amsterdam, NL, vol. 106, No. 3-4, May 12, 2009, pp. 150-165.

Lofgren M. et al: "Formation factor logging by electrical methods. Comparison of formation factor logs obtained in situ and in the laboratory", Contaminant Hydrology, vol. 61, No. 1-4, Mar. 1, 2003, pp. 107-115.

Marry V. et al: "Structure and dynamics of water at a clay surface from molecular dynamics simulation", Physical Chemistry Chemical Physics., vol. 10, No. 32, Jan. 1, 2008, p. 4802.

International Patent Application No. PCT/US2015/063576 International Search Report and Written Opinion dated Oct. 21, 2016 (20 pages).

* cited by examiner

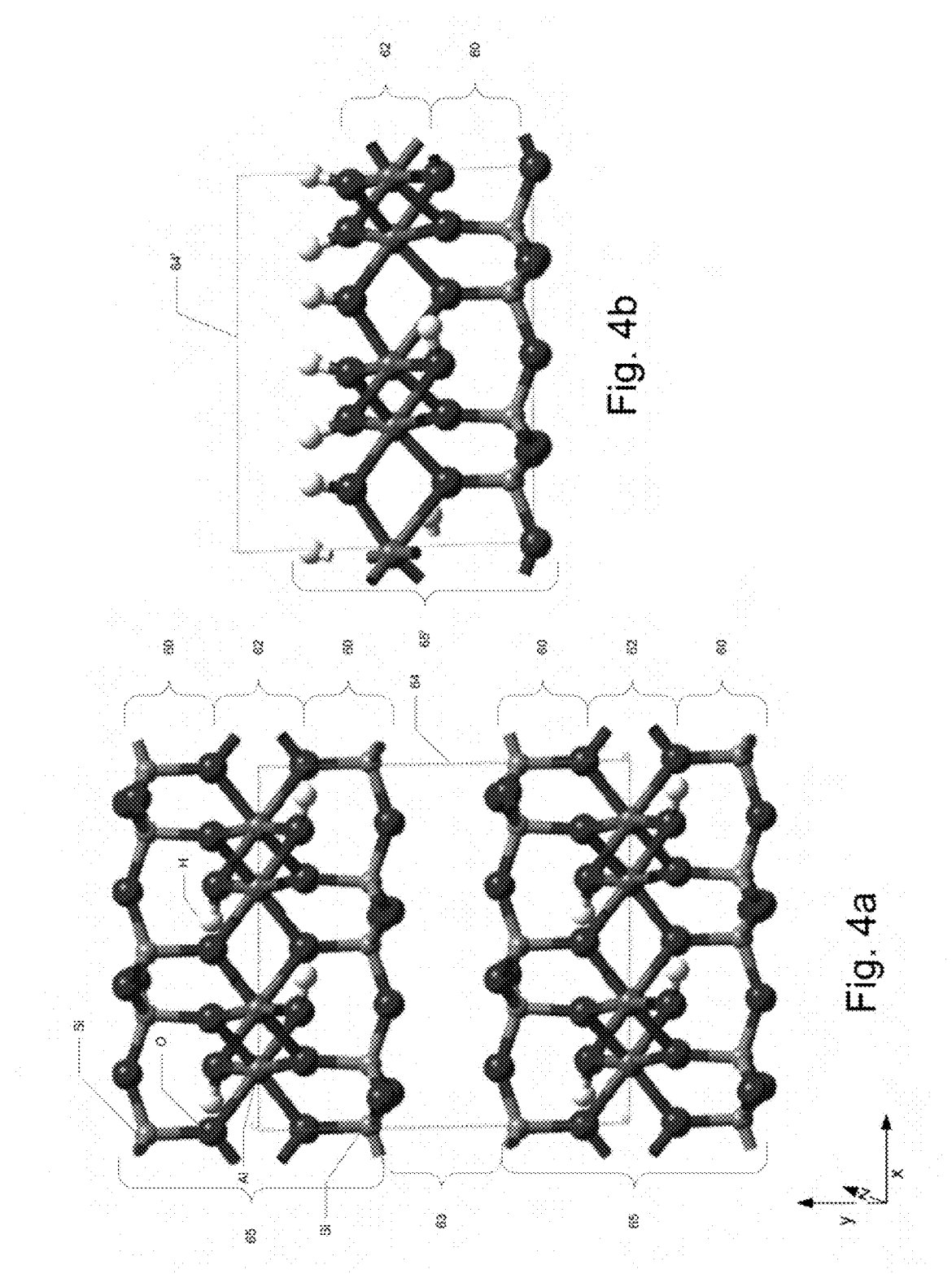

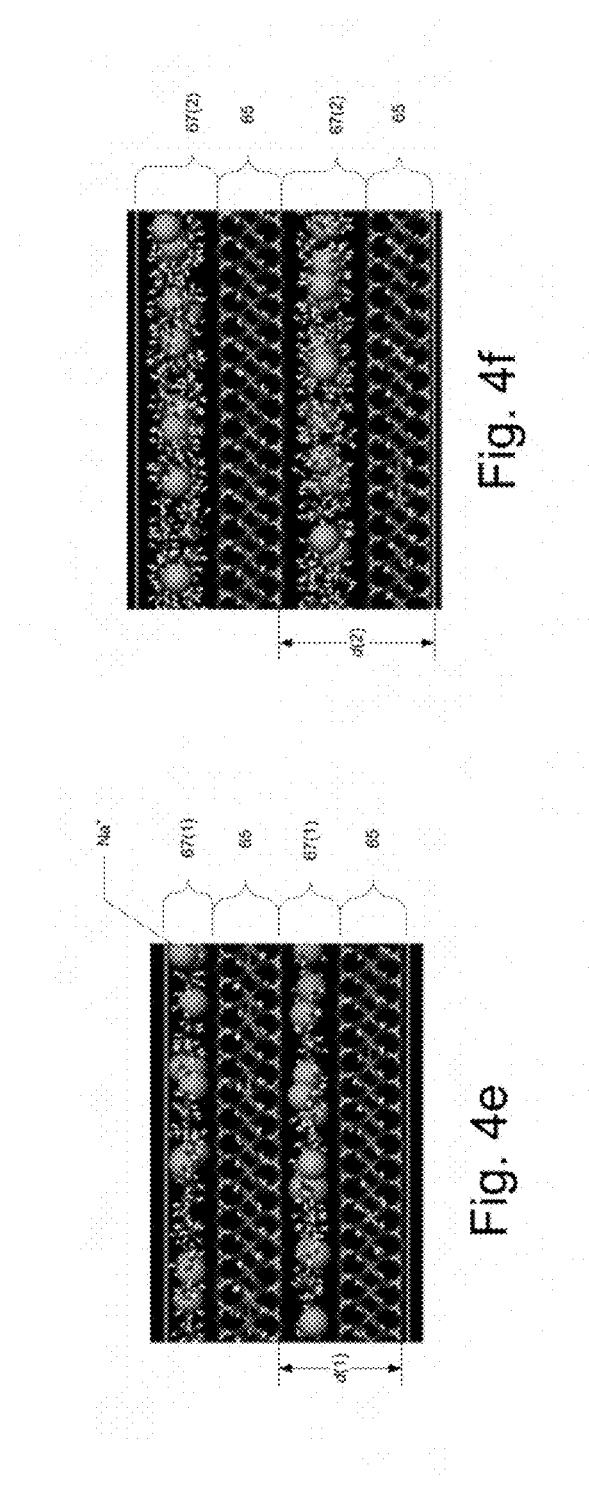
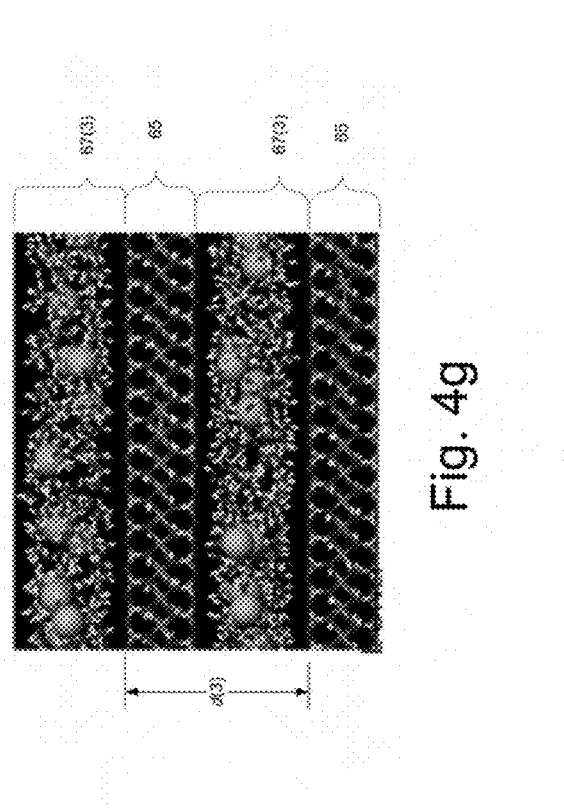
Fig. 4e
Fig. 4f
Fig. 4g

ESTIMATION OF CONDUCTIVITY FOR NANOPOROUS MATERIALS

STATEMENT REGARDING FEDERALLY SPONSORED RESEARCH OR DEVELOPMENT

The United States Government has rights in this invention pursuant to Contract No. DE-AC04-94AL85000 between the United States Department of Energy and Sandia Corporation, for operation of the Sandia National Laboratories.

CROSS-REFERENCE TO RELATED APPLICATIONS

Not applicable.

BACKGROUND OF THE INVENTION

This invention is in the field of analyzing rock samples to determine petrophysical properties.

As is fundamental in the oil and gas industry, the knowledge of the properties of the material of subsurface rock formations is important for assessing hydrocarbon reservoirs in the earth, and for formulating a development strategy regarding those reservoirs. A wide variety of tools and techniques for obtaining this information are well known in the art, and range from seismic data analysis, obtaining and analyzing core samples from the formations of interest, and various indirect measurements of the earth that are obtained during the drilling process.

A common technique for analyzing a sub-surface formation is resistivity logging along a borehole into the formation. Conventional resistivity logging measures the electrical response of the formation surrounding the borehole, typically to derive a value referred to as the "formation factor", which is the ratio of the resistivity of the fluid-bearing rock to the resistivity of the fluid itself. According to the well-known Archie's Relation, the formation factor is solely a function of the pore geometry of the rock, and can be correlated to porosity by way of an exponent referred to as the cementation exponent. As a result, analysis of a conventional resistivity log can provide important information regarding the porosity or water saturation of the formation of interest. In addition, resistivity logs in combination with the appropriate rock physics interpretation can provide insight into the permeability of the formation.

While Archie's Relation is commonly used to interpret electrical response from logs and from core samples, it was originally formulated based on a series of experimental measurements. It has been observed, however, that Archie's Relation is valid only for petrophysically simple rock formations, examples of which include clean sands. It has been further observed that Archie's Relation does not hold for shaly sands, namely sands containing clay minerals. A conventional approach for analyzing resistivity logs from shaly sands is referred to in the art as the Waxman-Smits Method. However, this approach is somewhat limited in practice, as it requires knowledge of the cation exchange capacity of the clay mineral in the shaly sand in order to correlate resistivity with water saturation and porosity.

The presence of clay within a rock sample has been observed to complicate the interpretation of electrical data obtained from logs and core samples. One reason for this is that the electrical properties of clay minerals (also referred to herein as "clays") are not well understood. In this regard, the interpretation of electrical properties (and associated properties such as cation exchange capacity) of clays as measured in the laboratory has proven difficult. This complicated interpretation of electrical data from clays also arises from the structure of typical clays being on the "nanoscale", which is much smaller than that of sands and which renders clays less amenable to atomic resolution experiments and analysis. In addition, the crystalline structure of clay minerals is often quite irregular, such as consisting of thin plates that are not oriented parallel to one another, with oddly-shaped boundaries and unusually-shaped pores. Furthermore, impurities that are often present in clays, particularly at external surfaces of the plates, can displace other atoms by substitution and change the charge distribution in the clay material. In general, these complexities of the nanoscale crystal size, the disorder of crystals and plates, and the complex composition of clay minerals render the direct measurement of petrophysical properties on clays very difficult.

Direct numerical simulation of material properties from digital images of rock is a recent technology for determining the material properties of rock samples. According to this approach, an X-ray tomographic image is taken of a rock sample to produce a digital image volume representative of that sample. A computational experiment is then applied to the digital image volume to simulate the physical mechanisms from which the physical properties of the rock can be measured. Properties of the rock such as porosity, absolute permeability, relative permeability, formation factor, elastic moduli, and the like can be determined using direct numerical simulation.

Specifically, direct numerical simulation of electrical properties from digital images of rock, is accomplished by approximating or solving relevant electrical equations such as the Laplace equation with variable coefficients and relevant boundary conditions. This approach assumes, however, that the electrical properties of constituent materials within the rock are known. For instance, solid grains (e.g., quartz) can be considered as nonconducting, clay fractions as partially conducting, and pore fluids such as brine as the most conducting phase in the simulation. While this assignment of conducting properties is well understood for solid grains and pore fluids, a physical basis for the assignment of the conductive properties to clays has not been established. As such, the use of assumed values for clay conductivity leads to uncertainties in conventional simulations of the electrical response of clay-bearing sands.

By way of further background, molecular dynamics ("MD") simulation refers to a computational method of describing the evolution, over time, of a finite molecular or atomic system, based on an approximate expression (i.e., a "force field") that determines the potential energy experienced by each atom in the system. In a conventional MD simulation, data such as coordinates, velocities, and forces for each atom under the force field are stored at periodic time intervals. These data are then used to calculate instantaneous and time-averaged properties, such as atomic or molecular trajectories, atomic or molecular density profiles in either one or two dimensions), interatomic structure (e.g., a radial distribution function), diffusion coefficients, vibrational structure, and the like.

BRIEF SUMMARY OF THE INVENTION

Embodiments of this invention provide a method and system of accurately estimating the electrical response of clay minerals and sands containing clay minerals.

Embodiments of this invention provide such a method and system for carrying out direct numerical simulation measurement of petrophysical properties upon a sample of a sub-surface formation that includes clay minerals.

Embodiments of this invention provide such a method and system for applying measurements, such as the direct numerical simulation measurement of the electrical response, of a nanoscale material such as a clay mineral or sands containing clay minerals, to a larger scale characterization of the formation.

Embodiments of this invention provide such a method and system for providing an estimate of formation factor for composite formations including nanoscale components such as clays.

Other objects and advantages provided by embodiments of this invention will be apparent to those of ordinary skill in the art having reference to the following specification together with its drawings.

Embodiments of this invention may be implemented into a method of simulating the electrical response of a clay mineral component, and a system of carrying out such a simulation. A model of a molecular clay system is constructed as a multi-layer structure corresponding to a clay mineral analogous to the clay of interest, with multivalent cations of a selected species inserted into the structure at a selected charge density, and with a number of water layers inserted into the interlayer space between layers in the structure, according to a selected water saturation. Force field parameters representing interatomic forces and simulation variables corresponding to the desired conditions of the simulation, such as pressure, temperature, volume, and the like, are assigned to the constructed model of the clay. Molecular dynamics simulation is then performed to determine diffusion coefficients of the interlayer ions in the clay system. Application of the Nernst-Einstein Relation then renders an estimate of the ion conductivities of the clay.

According to other embodiments of the invention, a method and corresponding system for performing direct numerical simulation of a rock containing clay fractions is provided. A three-dimensional (3D) image volume of a sample of the rock is obtained by X-ray tomography, followed by segmentation of the volume to differentiate the phases of non-conducting rock fractions (e.g., quartz), partially conducting fractions (e.g., clay), and pore space. Conductive properties are assigned to each segmented phase, and numerical simulation is performed to evaluate the electrical response of the volume. From the simulated response, one or more electrical properties of the corresponding clay-bearing rock sample are estimated.

According to other embodiments of the invention, a model of a molecular fluid system is constructed and populated with water at the desired density, with selected counterions interstitially placed in the model structure at the desired charge concentration. Force field coefficients are assigned to the model, and molecular dynamics simulation is performed to determine bulk fluid conductivity of the fluid as a reference. A formation factor for a clay-bearing material is then calculated from a ratio of the bulk conductivity of the reference fluid model to simulated ion conductivities of the clay system.

BRIEF DESCRIPTION OF THE SEVERAL VIEWS OF THE DRAWING

FIGS. 4a through 4g are schematic diagrams illustrating molecular models of clay mineral systems at various stages of the process of FIG. 3.

DETAILED DESCRIPTION OF THE INVENTION

This invention will be described in connection with one or more of its embodiments, namely as implemented into a method and system for developing simulations of clay minerals, particularly for use in connection with direct numerical simulation, as it is contemplated that this invention will be especially beneficial in such an application. However, it is contemplated that embodiments of this invention can provide significant benefits and advantages in a wide range of applications beyond those described herein. Accordingly, it is to be understood that the following description is provided by way of example only, and is not intended to limit the true scope of this invention as claimed.

In recent years, clays and shales have become important formations in the development and production of oil and gas. It has been observed that some of these clays have substitutional impurities such as aluminum atoms replacing silicon atoms in the crystalline structure, or magnesium or iron atoms replacing aluminum atoms in the crystalline structure. These cation impurities change the charge balance of the clay crystalline structure in such a way that adsorbed extraframework ions are required to maintain charge neutrality. These adsorbed extraframework ions are present on external surfaces of the clay, and are not part of the clay structure per se.

As described above, resistivity logs provide important information regarding the fluid content, fluid volume, and pore structure of sub-surface formations. However, the presence of clay components in the formation clouds the relationship between resistivity and the physical properties of interest, as both empirical and physics-based approximations of clay behavior exhibit large uncertainties. An improved understanding of the physical mechanisms involved in the conductivity behavior of clay minerals would therefore also be desirable.

Embodiments of this invention provide tools and techniques for gaining such an improved understanding of the physical mechanisms on which the behavior of clay minerals in sub-surface formations is based. In addition, as will be described below, these tools and techniques enable larger scale analysis of clay-bearing formations, in a manner that provides improved accuracy in an efficient manner.

Computerized System

Figure 1:
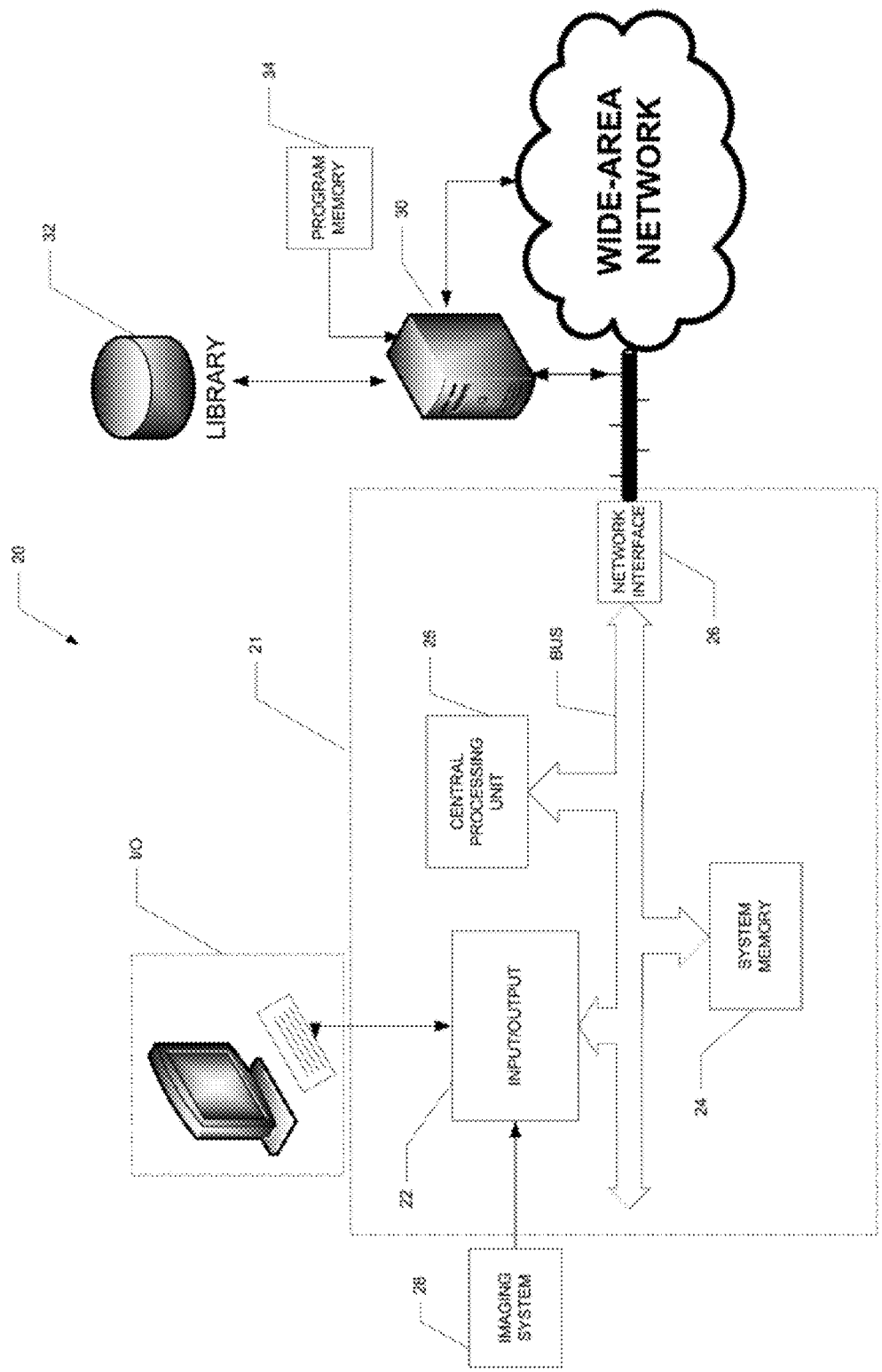
FIG. 1 is an electrical diagram, in schematic form, of a networked computer system programmed to execute various processes in the modeling and simulation of oil and gas reservoirs, according to embodiments of the invention.

According to embodiments of this invention, it is contemplated that these tools and techniques will be implemented, at least in part, by a computerized system, considering the nature and extent of calculations required. FIG. 1 illustrates an example of the implementation of an embodiment of the invention, in the form of computerized system 20, which performs the operations described in this specification to efficiently execute a simulation of the behavior of a clay mineral, particularly for purposes of estimating the conductivity of one or more clays, and in some embodiments for estimating the conductivity and other petrophysical properties of a rock sample including a clay component by way of direct numerical simulation. In this example, system 20 can be realized by way of a computer system including workstation 21 connected to server 30 by way of a network. Of course, the particular architecture and construction of a computer system useful in connection with this invention can vary widely. For example, system 20 may be realized by a single physical computer, such as a conventional workstation or personal computer, or alternatively by a computer system implemented in a distributed manner over multiple physical computers. Accordingly, the generalized architecture illustrated in FIG. 1 is provided merely by way of example.

As shown in FIG. 1 and as mentioned above, system 20 includes workstation 21 and server 30. Workstation 21 includes central processing unit 25, coupled to system bus BUS. Also coupled to system bus BUS is input/output interface 22, which refers to those interface resources by way of which peripheral functions I/O (e.g., keyboard, mouse, display, etc.) interface with the other constituents of workstation 21. Central processing unit 25 refers to the data processing capability of workstation 21, and as such may be implemented by one or more CPU cores, co-processing circuitry, and the like. The particular construction and capability of central processing unit 25 is selected according to the application needs of workstation 21, such needs including, at a minimum, the carrying out of the functions described in this specification, and also including such other functions as may be executed by system 20. In the architecture of system 20 according to this example, system memory 24 is coupled to system bus BUS, and provides memory resources of the desired type useful as data memory for storing input data and the results of processing executed by central processing unit 25, as well as program memory for storing the computer instructions to be executed by central processing unit 25 in carrying out those functions. Of course, this memory arrangement is only an example, it being understood that system memory 24 can implement such data memory and program memory in separate physical memory resources, or distributed in whole or in part outside of workstation 21. In addition, as shown in FIG. 1, workstation 21 can also receive from imaging system 28, via input/output function 22, data in the form of a digital image volume representative of a rock sample 28 from sensors and transducers deployed at wells in the production field. These measurement inputs can be stored in a memory resource accessible to workstation 21, either locally or via network interface 26.

Network interface 26 of workstation 21 is a conventional interface or adapter by way of which workstation 21 accesses network resources on a network. As shown in FIG. 1, the network resources to which workstation 21 has access via network interface 26 includes server 30, which resides on a local area network, or a wide-area network such as an intranet, a virtual private network, or over the Internet, and which is accessible to workstation 21 by way of one of those network arrangements and by corresponding wired or wireless (or both) communication facilities. In this embodiment, server 30 is a computer system, of a conventional architecture similar, in a general sense, to that of workstation 21, and as such includes one or more central processing units, system buses, and memory resources, network interface functions, and the like. According to this embodiment of the invention, server 30 is coupled to program memory 34, which is a computer-readable medium that stores executable computer program instructions, according to which the operations described in this specification are carried out by analysis system 20. In this embodiment of the invention, these computer program instructions are executed by server 30, for example in the form of an interactive application, upon input data communicated from workstation 21, to create output data and results that are communicated to workstation 21 for display or output by peripherals I/O in a form useful to the human user of workstation 21. In addition, library 32 is also available to server 30 (and perhaps workstation 21 over the local area or wide area network), and stores such archival or reference information as may be useful in system 20. Library 32 may reside on another local area network, or alternatively be accessible via the Internet or some other wide area network. It is contemplated that library 32 may also be accessible to other associated computers in the overall network.

Of course, the particular memory resource or location at which the measurements, library 32, and program memory 34 physically reside can be implemented in various locations accessible to system 20. For example, these data and program instructions may be stored in local memory resources within workstation 21, within server 30, or in network-accessible memory resources to these functions. In addition, each of these data and program memory resources can itself be distributed among multiple locations, as known in the art. It is contemplated that those skilled in the art will be readily able to implement the storage and retrieval of the applicable measurements, models, and other information useful in connection with this embodiment of the invention, in a suitable manner for each particular application.

According to this embodiment of the invention, by way of example, system memory 24 and program memory 34 store computer instructions executable by central processing unit 25 and server 30, respectively, to carry out the functions described in this specification. These computer instructions may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions for creating the model according to embodiments of this invention may be written in a conventional high level language such as JAVA, FORTRAN, or C++, either as a conventional linear computer program or arranged for execution in an object-oriented manner. These instructions may also be embedded within a higher-level application. More specifically, it is contemplated that the simulation of the behavior of the modeled sub-surface volume may be carried out, in part, by way of a computer simulation software application or package, an example of which is the Large-scale Atomic/Molecular Massively Parallel Simulator (LAMMPS) molecular dynamics computer software package available from Sandia National Laboratories, using a general force field framework suitable for molecular simulations, an example of which is the CLAYFF framework described in Cygan et al., "Molecular Models of Hydroxide, Oxyhidroxide, and Clay Phases and the Development of a General Force Field", *J. Phys. Chem. B*, Vol. 108 (2004), pp. 1255-1266, incorporated herein by reference. In any case, it is contemplated that those skilled in the art having reference to this description will be readily able to realize, without undue experimentation, this embodiment of the invention in a suitable manner for the desired installations. These executable computer programs for carrying out embodiments of this invention may be installed as resident within system 20 as described above, or alternatively may be in the form of an executable web-based application that is accessible to server 30 and client computer systems such as workstation 21 for receiving inputs from the client system, executing algorithms modules at a web server, and providing output to the client system in some convenient display or printed form. Alternatively, these computer-executable software instructions may be resident elsewhere on the local area network or wide area network, or downloadable from higher-level servers or locations, by way of encoded information on an electromagnetic carrier signal via some network interface or input/output device. The computer-executable software instructions may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by system 20 in the conventional manner for software installation.

Estimation of Ion Conductivity of a Clay Mineral

Figure 2:
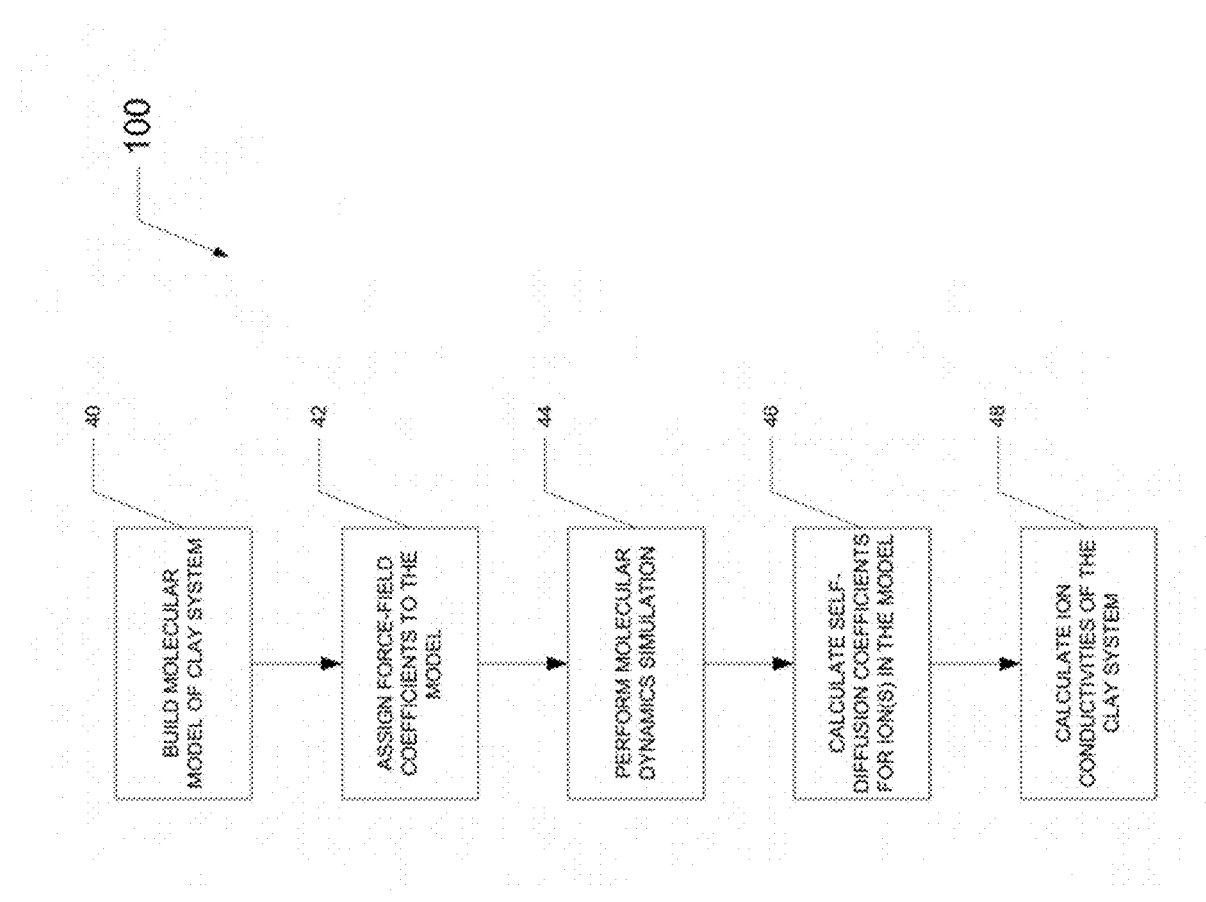
FIG. 2 is a flow diagram illustrating a process of estimating the ion conductivity of a clay mineral system, according to embodiments of the invention.
Figure 3:
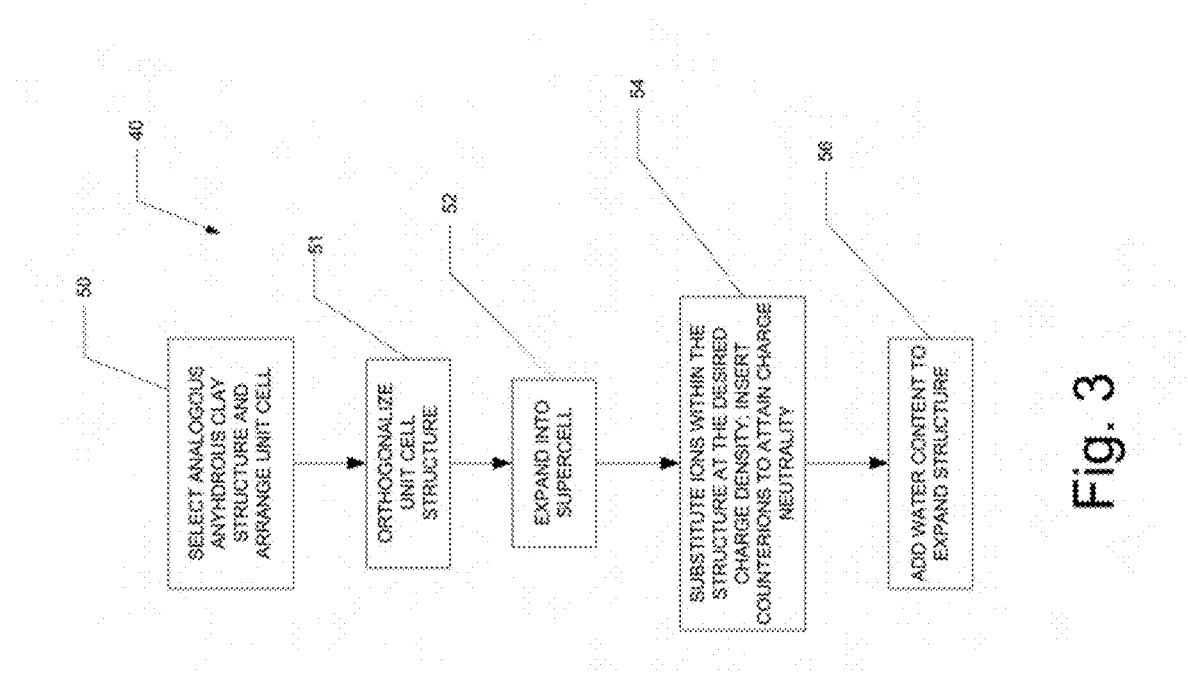
FIG. 3 is a flow diagram illustrating the construction of a molecular model of a clay mineral system in the process of FIG. 2, according to an embodiment of the invention.

FIG. 2 illustrates the generalized operation of system 20 in executing a simulation to estimate the conductivity of a modeled clay mineral system, typically corresponding to a component of a sub-surface formation of interest in the exploration and production of oil or gas, according to an embodiment of the invention. As mentioned above, it is contemplated that the various steps and functions in this process can be performed by one or more of the computing resources in system 20 executing computer program instructions resident in the available program memory, in conjunction with user inputs as appropriate. As mentioned above, it is contemplated that system 20 will be programmed, according to embodiments of this invention, with computer programs that, when executed by computing resources in system 20, will carry out the various processes described in this specification for simulation of the conductivity of clay mineral systems as specified by various physical parameter values and relationships.

While the following description will present an example of this operation as carried out at workstation 21 in the networked arrangement of system 20 shown in FIG. 1, it is of course to be understood that the particular computing component used to perform particular operations can vary widely, depending on the system implementation. As such, the following description is not intended to be limiting, particularly in its identification of those components involved in a particular operation. It is therefore contemplated that those skilled in the art will readily understand, from this specification, the manner in which these operations can be performed by computing resources in these various implementations and realizations. Accordingly, it is contemplated that reference to the performing of certain operations by system 20 will be sufficient to enable those skilled readers to readily implement embodiments of this invention, without undue experimentation.

As shown in FIG. 2, an initial step in estimating the conductivity of a clay mineral system according to embodiments of this invention is the construction of a molecular model of the clay system, in process 40. For purposes of this description, use of the term "molecular" in connection with the models of clay systems and conductivity estimation in this description is intended to refer to models and simulations in which individual atoms, ions, and molecules are represented; in that context, the term "molecular" is intended to be inclusive of atomic and ionic species, as well as molecules.

Referring now to FIGS. 3 and 4a through 4g, the operation of process 40 in constructing the molecular model of the clay mineral system to be simulated according to an embodiment of the invention will be described in further detail. Construction process 40 begins with process 50, in which an analogous anhydrous clay structure is constructed, in this example arranged according to a unit cell model. This analogous anhydrous clay structure is constructed to reflect the attributes of the clay mineral system to be modeled.

FIG. 4a illustrates an example of such an analogous anhydrous clay, from which a model of a smectite (swelling) clay will be constructed according to this embodiment of the invention. The analogous clay shown in FIG. 4a is based on muscovite as the analogous clay to the modeled smectite clay. Muscovite is referred to as a "2-1" layer aluminosilicate, in that each layer 65 of the clay consists of two silicate tetrahedral sheets on either side of a hydroxyl aluminate octahedral sheet (referred to herein as the aluminum octahedral sheet). According to this example, this muscovite structure is then modified by removing potassium ions from the octahedral sheet, and replacing aluminum atoms in the tetrahedral sheets with silicon atoms. This structure remains charge neutral and, in its anhydrous form, provides the structure of a pyrophyllite clay. FIG. 4a illustrates the structure of this pyrophyllite clay for portions of a pair of parallel clay layers 65, each including two silicate sheets 60 on either side of a single aluminum octahedral sheet 62. Unit cell 64 is shown in FIG. 4a, and serves as the basis for the model of this clay mineral system; the chemical formula for unit cell 64 in this example is $Si_8Al_4O_{20}(OH)_4$. The aluminum (Al), oxygen (O), hydrogen (H) and silicon (Si) atoms in the model of the pyrophyllite clay are labeled in FIG. 4a. As evident from this example of FIG. 4a, parallel layers 65 are separated from one another by "interlayer" space 63 (i.e., the gallery space between layers 65 in the structure); as will be described below, hydration of this clay structure will swell the volume of the clay, because one or more layers of water will be inserted into that interlayer space 63 between these parallel layers 65 of the structure.

FIG. 4b illustrates the unit cell structure for a different analogous clay mineral, namely kaolinite. Kaolinite is a "1-1" clay, in that a layer 65' (and thus a unit cell 64') of this clay includes one silicate sheet 60 and one aluminum octahedral sheet 62. As known in the art, kaolinite is not a smectite clay (i.e., does not have a permanent negative structural charge), and as such will not swell between its layers 65' upon hydration. Rather, the edges (i.e., ends) of kaolinite layers 65' are reactive, and as such are the sites of interaction with oil and water molecules.

It is contemplated that embodiments of this invention can be used to simulate conductivity in these, and other, clay structures. For purposes of this description, the clay structure of FIG. 4a will be discussed by way of example. It is contemplated that those skilled in the art having reference to this specification will be readily able to apply the methods and systems described herein, without undue experimentation, to the kaolinite clay of FIG. 4b, and to other clays of interest.

Referring back to FIG. 3, and according to this embodiment, once the unit cell structure is defined in process 40, process 51 is then performed to orthogonalize that unit cell 64 into a regular structure, with coordinates assigned to each of the atoms to indicate their positions in a coordinate system. Orthogonalization process 51 is optional, as the subsequent simulation processes described herein can be applied to the original mineral symmetry structure system (i.e., which may be non-orthogonal). However, it is contemplated that the subsequent processing is more conveniently applied to orthogonal model systems, as produced by process 51. Following orthogonalization according to this embodiment, unit cell 64 is expanded into a "supercell" in process 52. This supercell created in process 52 is made up of a number of such unit cells 64, and is of a size sufficient for the simulation processes described herein. For example, unit cell 64 of FIG. 4a may be expanded in process 52 into a supercell of sixty-four unit cells, arranged 8×4×2 in the x, y, and z directions (according to the orientation of FIG. 4a), respectively. The number of unit cell repetitions in each direction may of course vary, according to the desired simulation. Each of the atoms in the supercell representation will be assigned coordinates representing its position in the coordinate system.

Figure 4C:
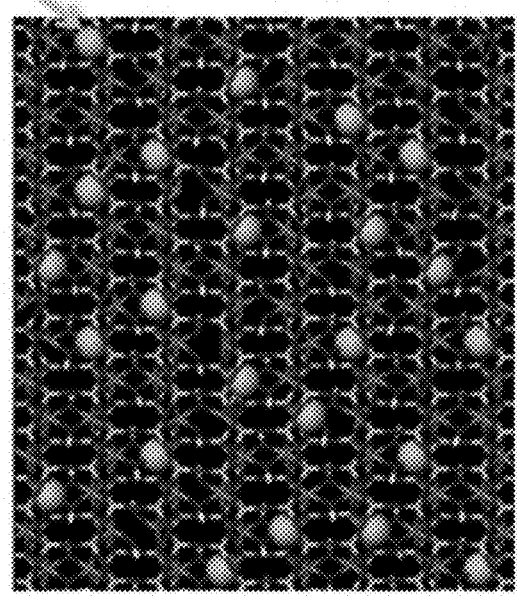
Figure 4D:
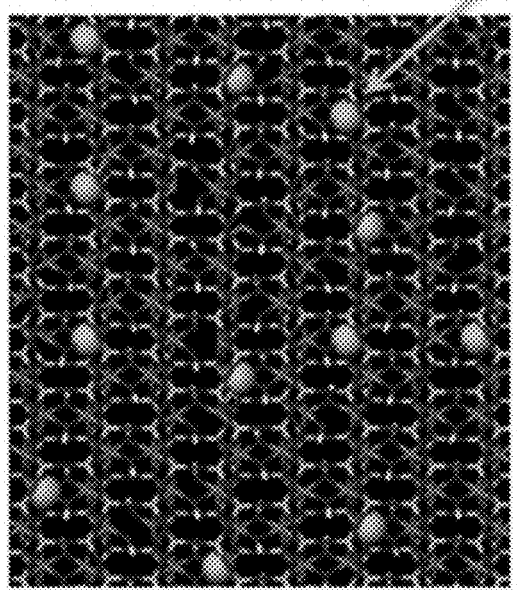

In process 54, according to this embodiment of the invention, ions of a selected species are substituted into the supercell structure, according to the desired charge density of the clay to be simulated. In this embodiment of the invention, a montmorillonite smectite clay is to be simulated. As such, magnesium ions are substituted for aluminum ions in the octahedral sheet 62 of the supercell structure, typically in random fashion. As known in the art, the charge of magnesium ions ($Mg^{2+}$) differs from that of the aluminum ions ($Al^{3+}$) being replaced, which results in negative charge sites at the locations of the supercell at which the magnesium ions reside. FIGS. 4c and 4d illustrate examples of supercells of the montmorillonite smectite clay based on the structure of FIG. 4a, in which magnesium ions are randomly substituted for aluminum ions at two different charge concentrations; these views of FIGS. 4c and 4d are plan views relative to the cross-sectional view of FIG. 4a, and as such interlayer space 63 between the parallel layers of the clay is not visible. While the placement of these substituted ions is random, that placement is preferably controlled so as to avoid the creation of nearest-neighbor Mg—O—Mg interactions. FIG. 4c illustrates a relatively low charge example, in which the net charge density of the supercell following substitution process 54 is −0.375e per unit cell, where e is the elementary electron charge; negative charge sites 66 are illustrated in this FIG. 4c at locations corresponding to the locations of the substituted magnesium ions. FIG. 4d illustrates a high charge example, in which the net charge density of the supercell following ion substitution process 54 is −0.750e per unit cell, which is twice the density of negative charge sites 66 as in the example of FIG. 4c. As part of ion substitution process 54, the supercell model is further modified by inserting counterions into the interlayer region to render the supercell charge neutral. In this example, either sodium or calcium counterions are used, although other counterion species may alternatively be used. In the examples of FIGS. 4c and 4d (i.e., with varying charge density), the resulting unit cell chemical formulae resulting from process 54, using sodium counterions, are $Na_{0.375}Si_8Al_{3.625}Mg_{0.375}O_{20}(OH)_4$ and $Na_{0.75}Si_8Al_{3.25}Mg_{0.75}O_{20}(OH)_4$, for the low and high charge density cases respectively.

In process 56, the clay supercell model structure is then hydrated by the introduction of water molecules into the interlayer space between clay layers in the supercell structure. For the example of the montmorillonite clay structure of FIG. 4a, hydration process 56 separates the 2-1 clay layers by inserting water molecules into interlayer space 63 between layers 65. In this embodiment of the invention, the introduction of water molecules in process 56 inserts these water molecules in the form of an integer number of layers of water molecules, according to the desired water concentration to be simulated. For example, one, two, or three layers of water may be inserted into interlayer space 63, yielding stoichiometric ratios of 3.9, 7.9, and 11.8 water molecules per unit cell, respectively. In one example, process 56 is performed by moving the counterions ($Na^+$, $Ca^{+2}$) inserted in process 54 into interlayer spaces 63, at locations above or below the corresponding negative charge sites 66 as the case may be, followed by then filling the remaining volume of interlayer spaces 63 with the corresponding number of water molecules at the desired concentration. This insertion of water molecules has the effect of increasing the separation between parallel layers of the 2-1 clay structure, and as such is representative of the swelling of the clay expected for smectite clays of this type.

FIGS. 4e through 4g illustrate the clay supercell model of FIG. 4a after hydration process 56, with varying numbers of water layers inserted between layers 65. FIG. 4e illustrates the arrangement of the clay supercell with one water layer 67(1) inserted between parallel layers 65 of the 2-1 clay structure. As evident from FIG. 4e, sodium ($Na^+$) counterions are retained within water layers 67(1). The resulting separation between adjacent parallel layers 65 defines the layer pitch d(1) for the case of one water layer 67(1). For purposes of this description, "pitch" refers to the combined thickness of one layer 65 and its adjacent interlayer space 63; this clay layer pitch can be considered as equivalent to the basal d-spacing as measured experimentally by X-ray powder diffraction methods. FIG. 4f illustrates the arrangement of the supercell with two water layers 67(2) inserted between each pair of parallel layers 65 of the 2-1 clay; the layer pitch d(2) in this case is greater than pitch d(1) for the single water layer case of FIG. 4e. FIG. 4g illustrates the supercell arrangement with three water layers 67(3) between each pair of adjacent parallel layers 65; the layer pitch d(3) in this three water layer case is again greater than pitch d(2) for the two water layer case.

As shown in FIGS. 4e through 4g and as mentioned above, the counterions (e.g., $Na^+$) are retained within the inserted water layers 67. The number and charge density of these counterions is determined by the number of the substitutions ($Mg^{2+}$ in this example) in clay layers 65 in the anhydrous structure defined in process 50, and as such does not vary with the number of water layers 67 inserted into the supercell representation. Because counterions ($Na^+$ or $Ca^{2+}$, as the case may be) are located within water layers 67, these counterions will be mobile under the appropriate stimulus (although it is believed that interactions between the counterions and neighboring water molecules will cause movement of both). As such, it is this movement of these counterions that give rise to the observed electrical conductivity in the clay in response to an applied potential. The simulation of the ion conductivity of this clay structure according to embodiments of this invention will thus determine the movement of these counterions to estimate the ion conductivity of the clay mineral system.

Coordinates of the atoms in the supercell structure after hydration process 56 has expanded the separation between adjacent layers 65, including coordinates for the counterions, are then stored as a representation of the constructed molecular model in the appropriate format within the memory of system 20. The construction of the molecular model of the clay system to be simulated in process 40 is then complete. Although the supercells in FIGS. 4e through 4g represent finite-sized models, in common practice periodic boundary conditions are used to effectively represent an infinite number of repeating supercell units in the x, y, and z directions. In this manner, long-range electrostatic interactions will be properly included in subsequent MD simulations, such as described below.

Referring back to FIG. 2, process 42 is then performed on the molecular model constructed in process 40. Process 42 assigns force field parameters to the constituents (atoms, molecules) of the constructed model and to their interactions with one another. According to this embodiment of the invention, the force field framework for clays known as "CLAYFF", described in the Cygan et al. paper incorporated by reference above, allows a great deal of flexibility in the specification of interaction parameters among the atoms and molecules in the supercell model of hydrated montmorillonite clay constructed in process 40. In this embodiment of the invention, the assignment of these parameters in process 42 is contemplated to be executed by system 20 within the simulation software environment, such as within the LAMMPS molecular dynamics computer software package referred to above.

Values of force field parameters and simulation variables are assigned to the constituents of the constructed model in process 42. As described in the Cygan et al. article, the force field parameters include:
representations of atoms in the model as point charges at locations within a coordinate system, with complete translational freedom within the model structure;
energies for each atom-atom interaction in the system, including those for long-range (Coulomb's law) electrostatic interactions, and short-range (van der Waals forces) interactions, and cutoff distances for the same; and
bond angles, bond lengths, etc., for hydroxyl groups and water molecules.

In addition, process 42 may also assign values to certain simulation variables according to the desired conditions of the simulation to be executed, for example including:
boundary conditions representative of pressure, temperature, and volume;
thermodynamic ensemble of parameters; and
other coefficients pertinent to the molecular dynamics simulation, as will be understood by those skilled in the art having reference to this specification.

Once assigned, optimization of the parameters in the force field framework may be performed as desirable, and according to conventional techniques as described in the Cygan et al. article incorporated hereinto by reference. This optimization may be performed, for example, to provide an energy-minimized structure as described in that article. The application of these force-field coefficients in process 42 may result in changes in the coordinate positions of the various constituents of the supercell model; for example, it has been observed that the layer pitches d(1), d(2), d(3) have a slight dependence on temperature.

Following assignment of the force field coefficients in process 42, system 20 then executes program instructions to carry out molecular dynamics (MD) simulation process 44. As described above, MD simulation software packages suitable for use in performing process 44 are known in the art. An example of such a suitable MD software package is the LAMMPS software package available from Sandia National Laboratories, as noted above.

According to embodiments of this invention, MD simulation process 44 evaluates the dynamics of the constituents of the supercell molecular model constructed in process 40, under the values of the force-field parameters and simulation variables as assigned in process 42. A useful approach to MD simulation process 44 is to evaluate both short-range and long-range interactions (i.e., the applicable and appropriate equations of motion) among the model constituents at a number of time steps within a selected time interval, to derive the positional coordinates, velocities, and forces of those constituents over that interval.

In one example according to an embodiment of the invention, short-range (van der Waals) interactions were evaluated at short time intervals (e.g., 0.5 fsec) with a cutoff distance (e.g., 10.0 Å) applied for those short-range forces, beyond which those interactions are ignored in the simulation. In these simulations, periodic boundary conditions were applied, and long-range electrostatic interactions evaluated at longer time intervals (e.g., 1.0 fsec), using a particle-particle particle-mesh (PPPM) summation algorithm as described in Plimpton et al., "Particle-mesh Ewald and rRESPA for parallel molecular dynamics simulations", *Proceedings of the Eighth SIAM Conference on Parallel Processing for Scientific Computing* (1997), incorporated herein by reference. In this example, the model systems were thermally equilibrated using an initial 50 psec simulation in the microcanonical ensemble (i.e., particle number, volume, and potential energy) with velocity rescaling according to the desired temperature, followed by an additional 50 psec simulation in the canonical ensemble (i.e., particle number, volume, and Nose-Hoover thermostat temperature). Following these initial simulations, a production simulation over a much longer time period (e.g., 2500 psec) was performed in the isothermal-isobaric ensemble (i.e., particle number, pressure, and temperature, with the Nose-Hoover barostat pressure set to zero). In this simulation, the volume of the supercell was allowed to change in only the z direction (i.e., perpendicular to the clay layers in FIGS. 4e through 4g).

The results of simulation process 44 are then applied to process 46, in which self-diffusion coefficients D of selected molecules and atoms are calculated by system 20. Process 46 in this embodiment of the invention is based on movement of the selected atoms and molecules of interest over a selected period of time during the simulation. In the simulation of the smectite clay described above, diffusion coefficients D for sodium ($Na^+$) or calcium ($Ca^{+2}$) counterions, depending on which are present, and water molecules in the inserted water layers 67 are based on the positional coordinates of those atoms and molecules at a series of evaluation times within a selected time interval of the MD simulation of process 44. For the example of the 2500 psec production simulation in the isothermal-isobaric ensemble referred to above, process 46 may be based on the coordinates of the atoms and molecules stored in memory of system 20 every 2.0 fsec over from the final 2000 psec of that 2500 psec simulation.

Based on these stored coordinate positions of the ions and molecules of interest, self-diffusion coefficients D are calculated in process 46 from the mean-square-displacement of those ions and water molecules in the x-y plane parallel to the basal surface:

$$\langle \Delta x(t)^2 + \Delta y(t)^2 \rangle = 4Dt$$

where the brackets ⟨ ⟩ denote an ensemble average of the x and y displacement of the ion or molecule at a given time t. Displacement in the z direction is set to zero in this example, as there is negligible diffusion in that direction (i.e., only random movement due to kinetic energy occurs in the z direction in simulation process 44). The ensemble average displacement over time is evaluated for each of the selected counterions and water molecules in water layers 67 in interlayer space 63 of the supercell structure subjected to the simulation, for example over only a sub-interval of the time over which the simulation was performed. In the above-described example, ion and molecule displacement was evaluated over the sub-interval from 200 psec to 800 psec points in the 2000 psec interval for which the coordinates were stored, to avoid the effects of nonlinear short-range (i.e., rotational) motion. From these results, the appropriate regression analysis (e.g., least-squares) can be performed to recover the slope of displacement versus simulation time, and thus the self-diffusion coefficient D for each species.

Alternatively, the diffusion coefficients for the ion and molecule species of interest in bulk fluids or in fluid-only simulations may be calculated in process 46, for example by directly calculating diffusion coefficient D from the three-dimensional trajectory of the ions and molecules:

$$D = \frac{1}{6} \lim_{t \to \infty} \frac{d}{dt} \sum_i \langle [r_i(t) - r_i(t_0)]^2 \rangle$$

where the brackets ⟨ ⟩ denote an ensemble average of the displacement of the ions or molecules over the time interval from the start time $t_0$ to time t. As such, this expression calculates the diffusion coefficient from the mean square displacement of the ions and molecules, as determined by MD simulation process 44.

According to embodiments of this invention, once the self-diffusion coefficients D for the species of interest are determined in process 46, ion conductivities of those species in the modeled clay system are calculated, for example by system 20, in process 48, by the application of the Nernst-Einstein relationship. Discussion of the Nernst-Einstein relationship can be found in Bockris et al., *Modern Electrochemistry 1: Ionics*, 2$^{nd}$ ed. (Plenum Press, New York, 1998), pp. 456-458, incorporated herein by reference. More specifically, according to embodiments of the invention, the ion conductivity for the counterion species of index i (referring to the one of Na$^+$ or Ca$^{2+}$ included in the model according to the example described above) entrained in water layers 67 may be calculated from its self-diffusion coefficient $D_i$ as follows:

$$\sigma_i = \frac{z_i^2 c_i F^2 D_i}{RT}$$

where $z_i$ is the ion valency of counterion i, $c_i$ is the ion concentration of counterion i, F is the Faraday constant, R is the gas constant, and T is the temperature. Similarly, the molar ion conductivity $\lambda_i$ can be calculated:

$$\lambda_i = \frac{\sigma_i}{c_i} = \frac{z_i^2 F^2 D_i}{RT}$$

According to embodiments of this invention, therefore, ion conductivity in a modeled clay mineral system can be estimated based on a molecular model of that clay system. This simulation process can be readily repeated for different counterion species, varying levels of hydration (i.e., different numbers of water layers 67 between clay layers 65), varying physical conditions (e.g., temperature, pressure, etc.), and varying charge densities, and the like. Analysis of the results from the resulting ensembles can provide insight into the conductivity mechanisms, and can also assist experimental confirmation of the simulation results. In addition, the ability of this simulation tool to estimate conductivity over a wide range of conditions can develop empirical relationships that are useful in the understanding of petrophysical properties of sub-surface formations.

Estimation of Formation Factor of a Clay Mineral System

As mentioned above, a petrophysical property that is often of particular interest in connection with the analysis of resistivity logs, as commonly obtained in the exploration and production of oil and gas reservoirs, is referred to as the "formation factor". The common definition of formation factor is a ratio of the resistivity of the formation rock to the resistivity of the fluid itself.

Figure 5:
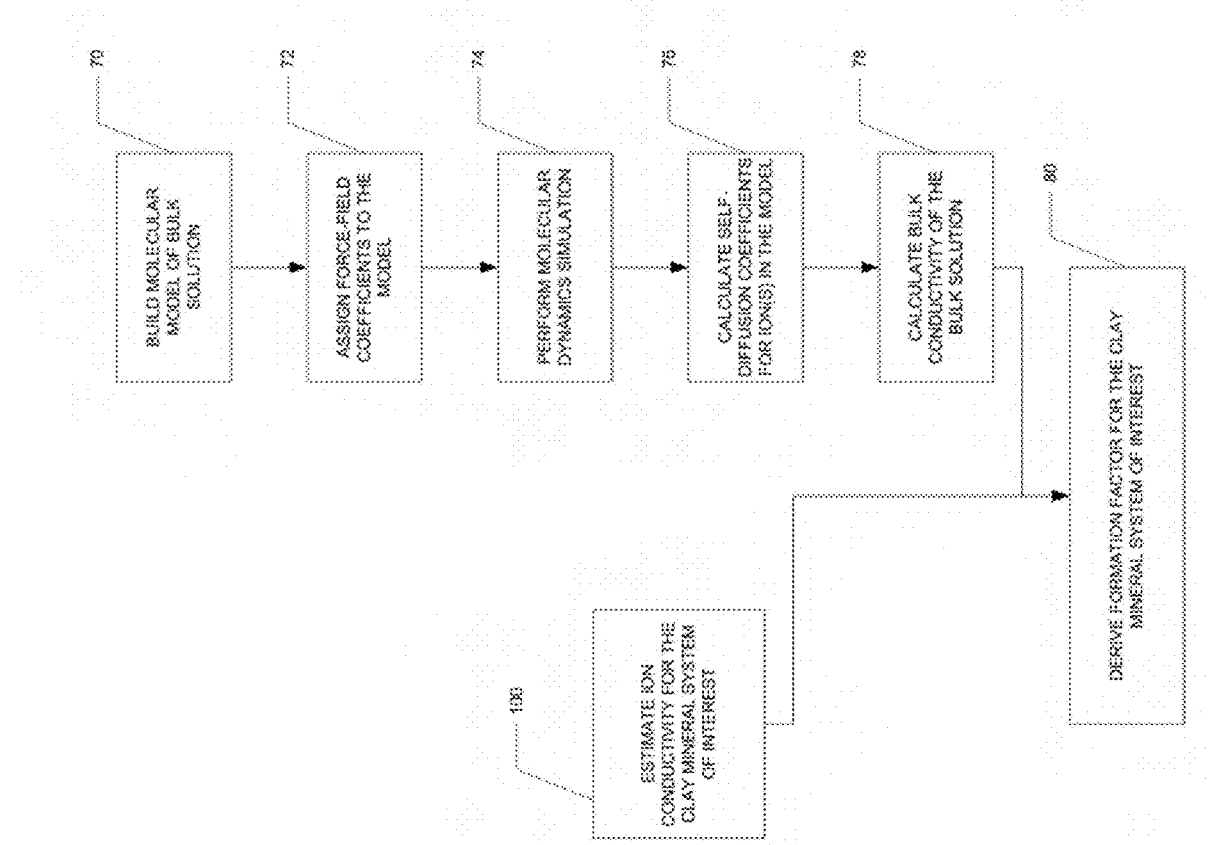
FIG. 5 is a flow diagram illustrating a process of estimating formation factor for a clay mineral system, according to an embodiment of the invention.

FIG. 5 is a flow diagram of this process of estimating the formation factor for a particular clay mineral system. As shown in FIG. 5, the ion conductivity for this clay mineral system is determined by system 20 in process 100, according to the process described above in connection with FIG. 2. In order to derive the formation factor, however, the bulk conductivity of the fluid is also necessary. According to this embodiment of the invention, that bulk conductivity is estimated in similar fashion as the ion conductivity of the clay system, beginning with process 70.

In process 70, a molecular model of a bulk (i.e., neutral charge) solution representative of the desired fluid is constructed. For example, process 100 described above is applied to a model in which Na$^+$ or Ca$^{2+}$ cations were entrained in the injected water layers 67 along with Cl$^-$ anions to maintain charge neutrality. In that example, the molecular model of the bulk solution contains 4096 molecules of water, four cations of sodium (Na$^+$) or calcium (Ca$^{2+}$), and four or eight Cl$^-$ anions (as the case may be), in a cube of approximately 50 Å on a side. The molar cation concentration in this modeled bulk solution is thus about 0.05.

Alternatively, if the corresponding bulk solution modeled in process 70 does not include anions and thus has a net positive charge, a charge-compensating background may be inserted into the model to maintain charge neutrality.

Process 72 through 76 are then performed on the molecular model of the bulk solution constructed in process 70, in similar fashion as processes 42 through 46 described above for the clay mineral system. In summary, the force field parameters assigned to the molecules and cations in the bulk solution model in process 72 specify such parameters as locations of the atoms within a coordinate system and energies of the molecules and atoms, and the simulation parameters include boundary conditions representative of pressure, temperature, and volume, thermodynamic ensemble of parameters, and the like. In process 74, a molecular dynamics (MD) simulation is executed by system 20 on this molecular model based on the specified force field coefficients, to determine the positions of the water molecules and cations over the simulation time, for example storing the location of each molecule and cation at a sample frequency of 2 psec over a 10 nsec simulation interval, under constant pressure and constant temperature simulation conditions. In process 76, self-diffusion coefficients are calculated for the cations and water molecules in the modeled bulk solution, based on the stored locations at the sample times within the MD simulation of process 74. In this process 76, the self-diffusion coefficients may be calculated similarly as in process 46 described above, based on the mean-square displacement in the x-y plane or based on an ensemble average from the ion trajectory in three dimensions.

Examples of the diffusion coefficient values calculated for a molecular bulk solution model according to the approach of processes 70 through 76 have been observed to agree well with reported results for the diffusion coefficients of sodium and calcium solutions at infinite dilution.

In process 78, the self-diffusion coefficient for the cation in the bulk solution model, at the temperature applied as a boundary condition in process 72, is then applied to the Nernst-Einstein relationship to determine the conductivity of the solution, as described above. This conductivity calculated in process 78 constitutes the bulk thus provides an estimate of the bulk conductivity of the fluid in the clay mineral system, from which the formation factor F of the clay mineral system of process 100 can be determined in the conventional manner, in process 80:

$$F = \frac{\sigma_b}{\sigma_i}$$

where $\sigma_i$ is the ion conductivity of the counterion in the modeled clay system determined in process 100, and $\sigma_b$ is the bulk conductivity of the bulk solution calculated in process 78. As known in the art and as described above, the formation factor F provides a good measure of the porosity in the formation structure, from which other important petrophysical properties such as permeability can be determined.

Accordingly, this embodiment of the invention provides the ability to estimate the formation factor value of a clay mineral system from the modeling and simulation of the relevant mechanisms at the molecular level. This molecular-level analysis enables accurate analysis of nanoscale formation components, beyond the capability of conventional approaches such as Archie's Relationship and the like.

Direct Numerical Simulation of Formations Including a Clay Component

The ability to accurately estimate conductivity of clay minerals provided by embodiments of the invention, as described above, can be helpful in a wide variety of petrophysical analyses, particularly considering the current importance of hydrocarbon-bearing rock formations that contain clay-bearing sands. In addition, it is also contemplated that the understanding of the physical mechanisms operating on the molecular level in these nanoscale materials will be particularly useful in the design and analysis of production technologies. Other analytical tools and techniques are also contemplated to be improved by the conductivity estimation techniques of embodiments of this invention.

One such analytical tool and technique that can be improved by an accurate estimate of the conductivity of clay mineral systems is direct numerical simulation, particularly as applied to sub-surface formations that include both a rock phase such as quartz, as in a sandstone, and a clay mineral phase. As known in the art, clay components in formations of this type are typically formed of a number of largely parallel plates; for example, the clay mineral kaolinite is typically in the form of "booklets" interspersed among the solid quartz grains and pore space. As discussed above in connection with the Background of the Invention, conventional resistivity logs interpreted according to Archie's Relation are based on the solid grains exhibiting effectively zero conductivity while fluid in the pore space exhibits high conductivity. In those formations in which this assumption is valid, the measured resistivity will provide a good indication of porosity of the formation. However, as known in the art, clay components in the formation will also exhibit conductivity, but to a lesser extent less than that of the pore fluid yet significantly greater than that of the solid quartz grains. Conventional resistivity analysis will therefore provide a generally ambiguous result when applied to a formation including clay components, since the resistivity will depend not only on the porosity as exhibited by pore fluid, but also on the extent to which clay components are present and their conductivity.

Figure 7:
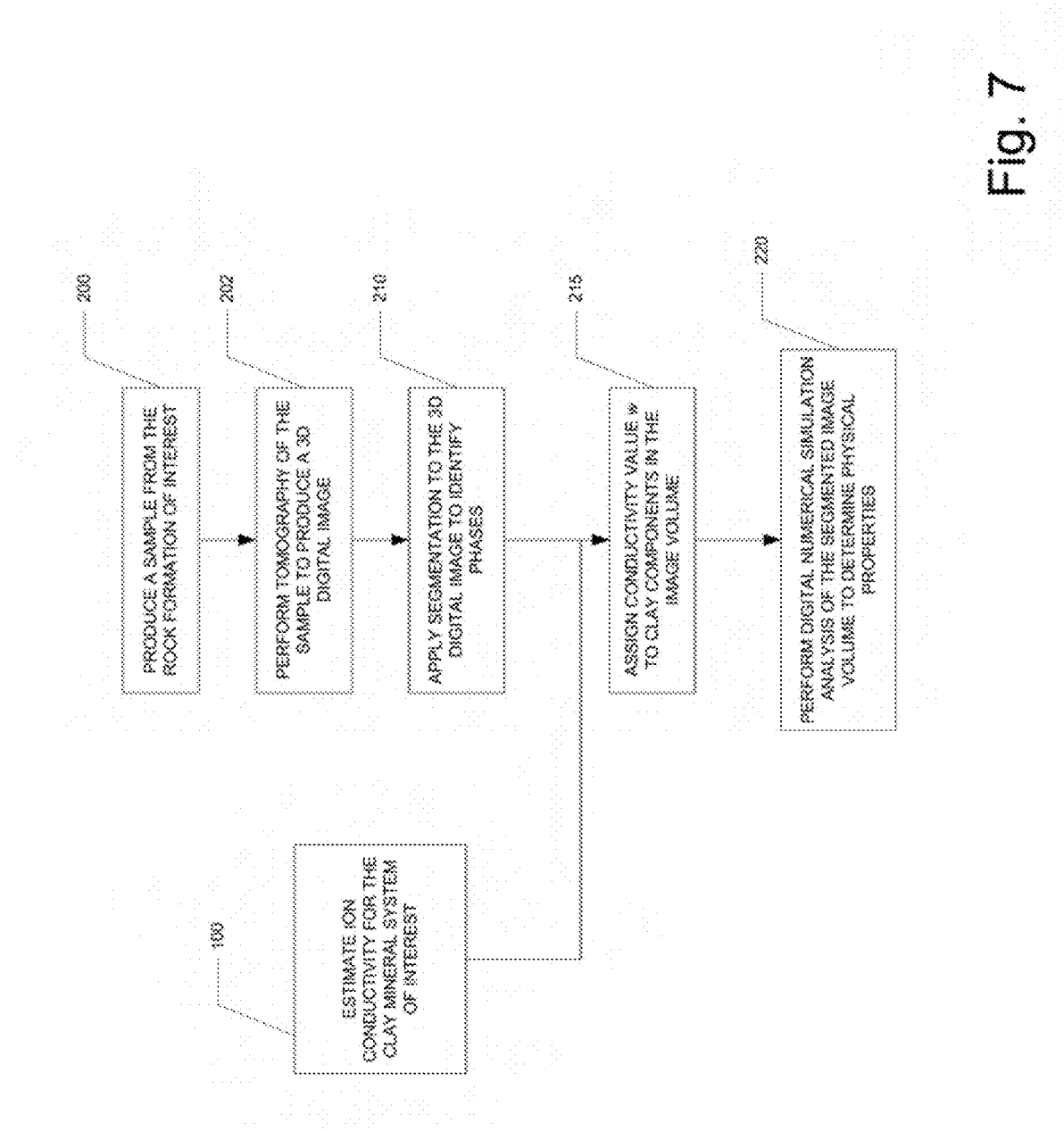
FIG. 7 is a flow diagram illustrating a process of performing direct numerical simulation on a sample of a composite formation such as shown in FIGS. 6a and 6b, for use in connection with resistivity logs and measurements, according to an embodiment of the invention.

According to an embodiment of the invention, the existence of an accurate estimate for the conductivity of clay components in a composite formation can be used when determining the electrical response by way of direct numerical simulation of an image volume of a rock. Referring now to FIG. 7, the overall process of the estimation of material properties using digital numerical simulation according to embodiments of this invention will be described.

The estimation process begins with sample preparation process 200, in which a specimen of the formation of interest is obtained, and a sample of that specimen prepared for analysis. The specimen of the formation may be acquired in any one of a number of conventional ways. In the context of the oil and gas industry, the specimen will typically be derived from the drilling of exploration or production wells, and as such may come from whole core samples, side wall core samples, outcrop samples, and drill cuttings; alternatively, the specimen may be produced from a laboratory generated synthetic rock sample such as a sand pack or a cemented pack. According to embodiments of this invention, the rock from which the specimen is obtained may not always be highly consolidated, as it will include a combination of rock (e.g., sandstone) along with clays, and other granular or sedimentary material. As such, preparation process 200 should be performed in a way that does not significantly disturb the structure of the formation to be represented by the sample.

In process 202, imaging system 28 (FIG. 1) obtains two-dimensional (2D) or three-dimensional (3D) images, or other appropriate image representations, of the rock sample prepared in process 200. These images and representations obtained in process 202 include details of the internal structure of the samples. An example of the imaging device used in process 202 is an X-ray computed tomography (CT) scanner, of a type, construction, or other attributes corresponding to any one of a number of X-ray devices capable of producing an image representative of the internal structure of the sample of the desired resolution. For example, a plurality of two-dimensional (2D) sectional images of the sample may be acquired, and forwarded to computer system 20 that then constructs a three-dimensional (3D) digital image volume corresponding to the sample. As discussed above, system 20 may be constructed in any one of a number of ways, for example, as a desktop computer or workstation, a laptop computer, a server computer, a tablet computer, or the like, with sufficient computational capacity to carry out the desired operations.

Specific conventional techniques for acquiring and processing 3D digital image volumes of the sample in process 202 include, without limitation, X-ray tomography, X-ray micro-tomography, X-ray nano-tomography, Focused Ion Beam Scanning Electron Microscopy, and Nuclear Magnetic Resonance.

The image volume produced by process 202 is typically represented by 3D regular elements called volume elements, or more commonly "voxels", each having an associated numeric value, or amplitude, that represents the relative material properties of the imaged sample at that location of the represented medium. In process 210, the computing device performs segmentation or other image enhancement techniques on the digital image volume of the sample to distinguish and label different components in the image volume. For example, segmentation process 210 may identify the significant elastic components, including pore space and mineralogical components (e.g., clays and quartz), that can affect the characteristics of the sample.

According to this embodiment of the invention, segmentation process 210 is then performed by system 20 to identify the significant material phases of the sample represented in the image volume, for example representing such material constituents as pore space, clay fractions, and individual grains and minerals. The particular segmentation algorithm used by the computing device in process 210 may vary according to the analysis desired and the complexity of the rock. The simplest form of segmentation is "thresholding", which groups voxels having similar amplitudes with one another. Conventional image processing to enhance the image volume, to reduce noise, etc. may be included in process 210.

Figure 6A:
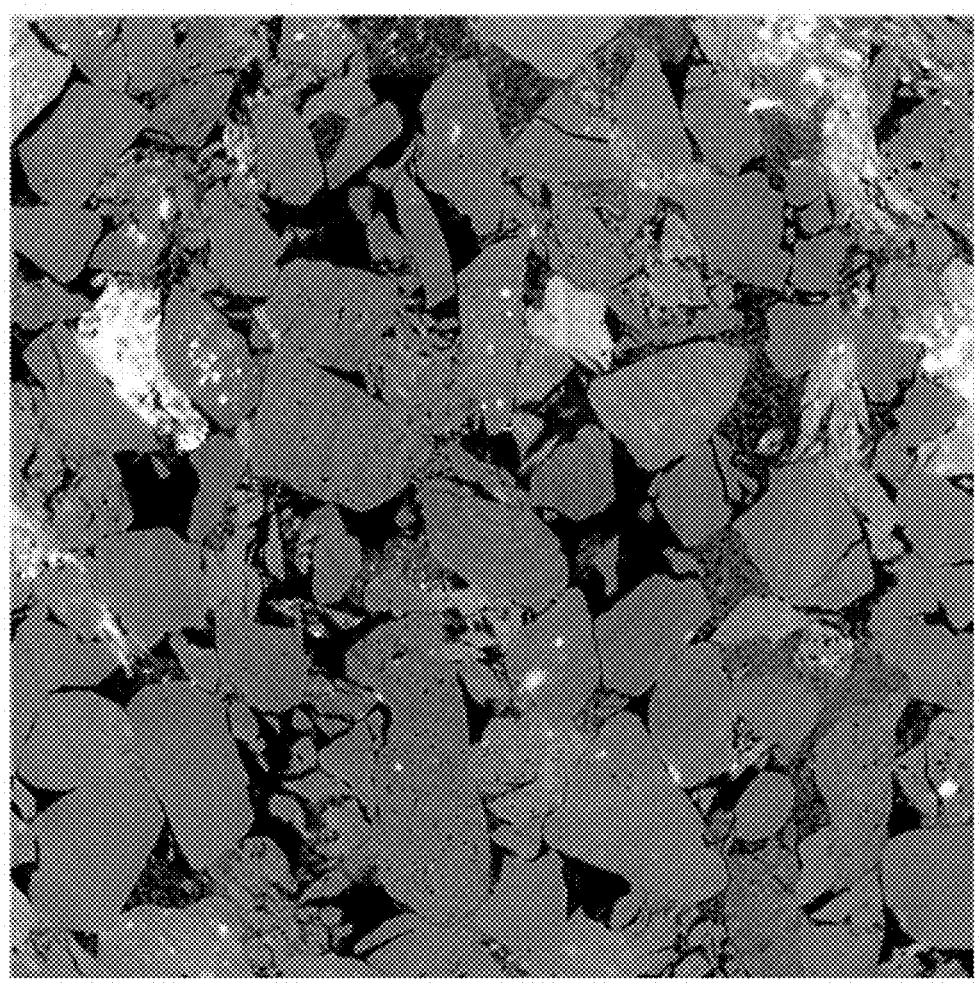
FIGS. 6a and 6b are an X-ray microtomography image and a segmented representation, respectively, of a sample of a composite formation including a clay component, for analysis according to embodiments of the invention.
Figure 6B:
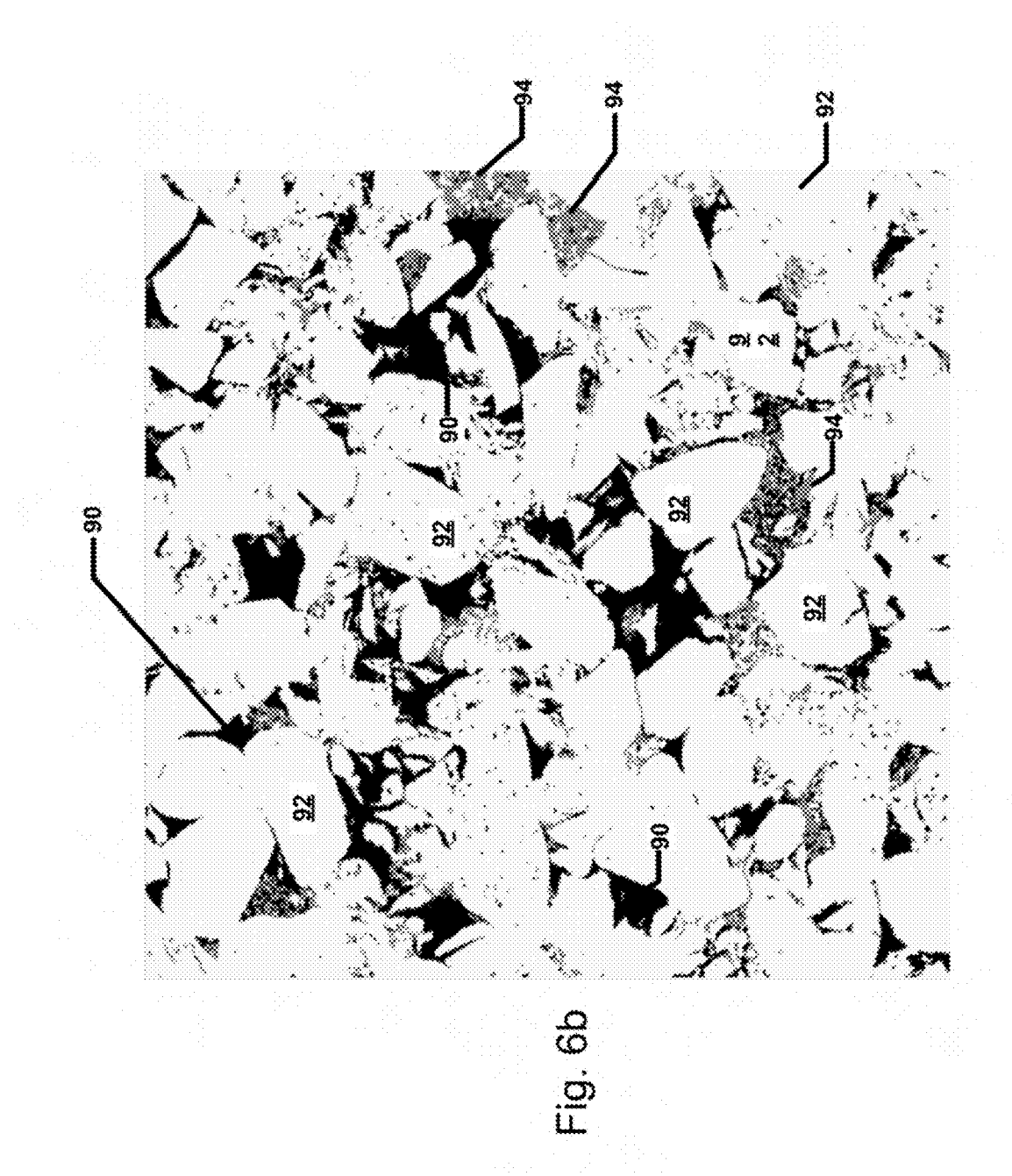

According to this embodiment of the invention, segmentation process 210 identifies and distinguishes at least three significant material phases, namely pore space, rock grains, and clay minerals. An example of the operation of segmentation process 210 is shown by FIGS. 6a and 6b. FIG. 6a is an example of an X-ray microtomography image of a sandstone rock containing clay mineral components, such as kaolinite, along with its solid quartz grains. In the image of FIG. 6a, pore space corresponds to the black regions, while the quartz grains and clay components correspond to the varying intermediate shades of grey (the lighter grey tending to indicate the quartz grains). Typically, the spatial resolution of an X-ray microtomography image such as FIG. 6a ranges from 1 to 5 microns, which means that the texture, configuration and fabric of clay minerals are not observable at this scale. In addition, the brightness varies somewhat continuously in the image of FIG. 6a, which renders numerical analysis complex and difficult. Segmentation process 210 operates to distinguish pore space, solid grains, and clay components from one another. FIG. 6b illustrates an example of the results of segmentation process 210 applied to the X-ray microtomography image of FIG. 6a, in which three phases are represented as black for pore space 90, white for quartz or other solid grain material 92, and an intermediate grey for clay components 94. In general, as mentioned above, segmentation process 210 is applied to the 3D image volume acquired in process 202.

According to this embodiment of the invention, an estimate of the conductivity for clay components 94 is derived in process 100. As discussed above, it is contemplated that process 100 described above in connection with FIG. 5 will provide an excellent estimate of conductivity for clay component 94 in the sample prepared and imaged in processes 200 and 202. However, it is also contemplated that other approaches for measuring and estimating conductivity in clay component 94 may alternatively be used in connection with this embodiment of the invention; it is expected, however, that conventional approaches to estimating conductivity of clay mineral systems are less rigorous, and will generally provide less accurate estimates of conductivity, than that described above in connection with embodiments of the invention.

Based on the estimate of conductivity derived in process 100, process 215 is then performed to assign a relative conductivity value w to clay components 94 in the segmented image volume. As discussed above, quartz crystals 92 (or other solid material) exhibit effectively zero conductivity in conventional resistivity analysis while fluid in pore space 90 exhibits high conductivity; clay components 94 are typically conductive, as estimated in process 100, but to a lower extent than fluid in pore space 90. According to this embodiment of the invention, the relative conductivity value w assigned to clay components 94 in process 215 reflects the estimated conductivity of clay as compared with that of the fluid. The formation factor F calculated as described above can be the basis of this relative conductivity value w, for example. This relative conductivity value w is then assigned to each of the voxels representing clay components 94 in the segmented digital image volume from process 210. Of course, if clay components 94 in the image volume represent more than one species of clay, separate conductivity estimates for those different clay phases may be estimated in process 100, and applied by way of different relative conductivity values w in process 215.

Figure 6C:
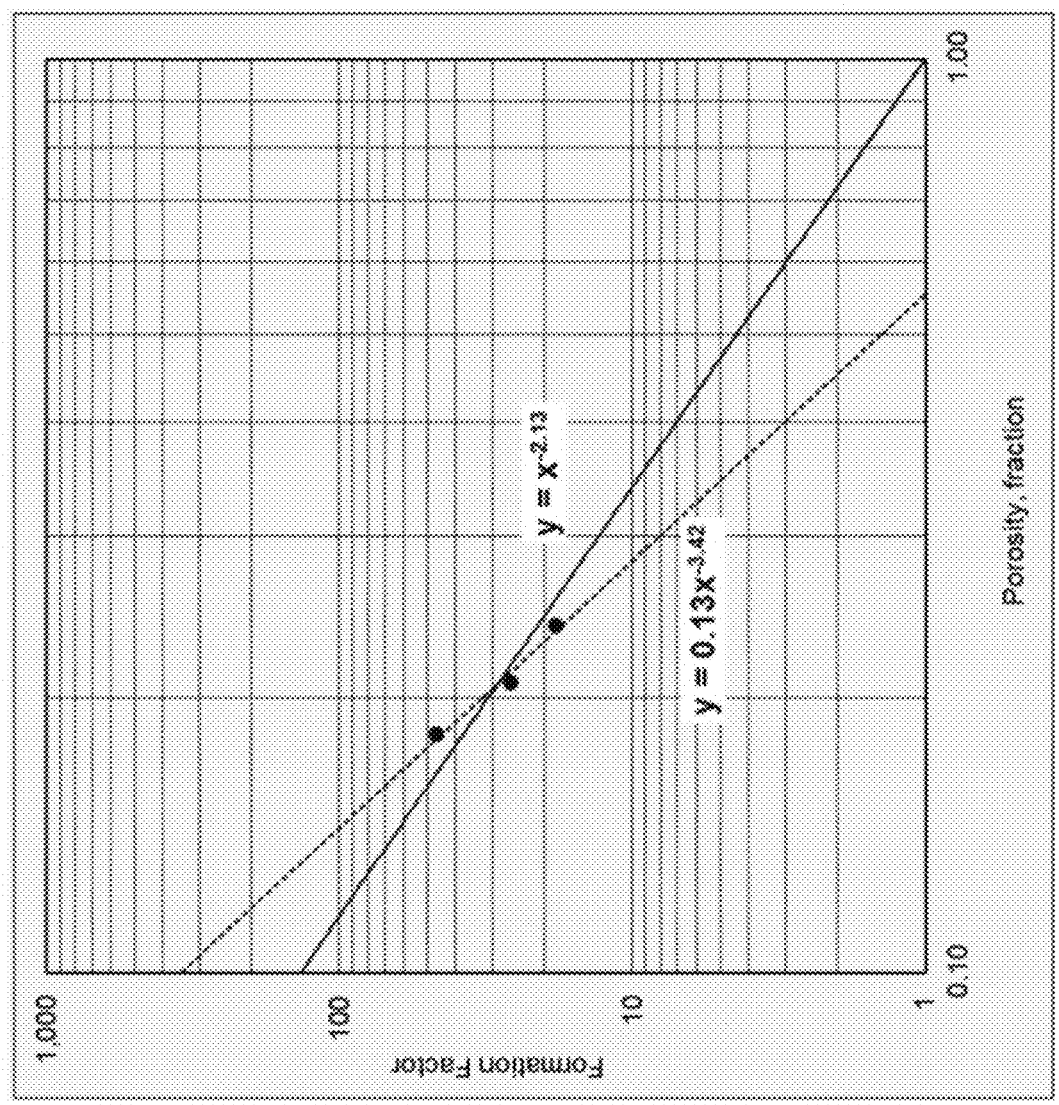
FIG. 6c is a plot of formation factor for three different clay-bearing sands using direct numerical simulation, according to an embodiment of the invention.

In process 220, computing system 20 then performs direct numerical simulation to analyze one or more physical properties of the sample, typically by way of numerical analysis of the segmented digital image volume. The properties that may be determined in process 220 include those petrophysical properties of interest that directly or indirectly relate to the conductivity of clay components 94, such as porosity, formation factor, cementation exponent, resistivity index, tortuosity factor, saturation exponent, and the like. These petrophysical properties may be estimated using an appropriate discretization of the entire segmented digital image volume or mesh of the evolved pore space and clay components, combined with appropriate numerical simulation, e.g. the direct numerical simulation of electrical conductivity for determining the electrical properties of the rock. The determination of some of these petrophysical properties in process 220 may also require numerical simulation using finite element methods, finite difference methods, finite volume methods, Lattice Boltzmann methods or any variety of other numerical approaches. For example, FIG. 6c illustrates computation of the formation factor for three different clay-bearing sands using direct numerical simulation, where the clay components 94 have assigned conductivities.

According to this embodiment of the invention, therefore, it is contemplated that conventional resistivity logs can be extended to more complex formation structures, including formations with clay mineral components, and provide accurate results about important petrophysical properties such as porosity, water saturation, clay fraction, and the like, particularly if the conductivity is estimated according to the embodiments of this invention described above. Analysis of the effects of secondary recovery processes on formations for which resistivity logs have been obtained, are also contemplated.

In Conclusion

As described above, embodiments of this invention provide a method and system of accurately estimating the electrical response of clay minerals and sands containing clay minerals, in a manner that is based on physical mechanisms taking place on the molecular level. The ability to analyze nanoscale materials such as clay minerals in this manner is contemplated to be useful over a wide range of clay structures, beyond the pyrophyllite, montmorillonite, and kaolinite examples specifically described above, as the same approach can be applied to a wide variety of molecular models for clay minerals. This ability can provide additional insight into other analytical tools, such as the direct numerical simulation measurement of petrophysical properties upon a sample of a sub-surface formation that includes clay minerals, and the development and analysis of formation factor for composite formations including nanoscale components such as clays.

While this invention has been described according to its embodiments, it is of course contemplated that modifications of, and alternatives to, these embodiments, such modifications and alternatives obtaining the advantages and benefits of this invention, will be apparent to those of ordinary skill in the art having reference to this specification and its drawings. It is contemplated that such modifications and alternatives are within the scope of this invention as subsequently claimed herein.

What is claimed is:

1. A method of operating a computer system to calculate electrical conductivity in a rock sample comprising a clay mineral, comprising:
    constructing a molecular representation of the clay mineral, comprising:
        an anhydrous structure of atoms arranged in a plurality of parallel layers, the anhydrous structure including substitution sites in place of metal atoms in the structure at a concentration corresponding to a selected charge density;
        counterions of at least one species disposed in an interlayer space between layers of the anhydrous structure, at a concentration corresponding to the selected charge density; and
        a plurality of water molecules disposed in the interlayer space;
    assigning force field parameters to the molecular representation in combination with boundary conditions corresponding to a selected pressure and temperature condition of the clay mineral;
    operating the computer system to perform a molecular dynamics simulation of equations of motion over a simulation time interval to determine positional coordinates of counterions in the representation at a plurality of times during the simulation time interval;
    calculating self-diffusion coefficients for one or more of the species of counterions from the positional coordinates at the plurality of times;
    calculating ion conductivities for a species of counterions from the self-diffusion coefficients;
    determining at least one petrophysical property of the rock sample based on the ion conductivities for the species of counterions; and
    assessing a hydrocarbon reservoir in earth based on the at least one petrophysical property of the rock sample.

2. The method of claim 1, wherein constructing the molecular representation comprises:
    defining a unit cell of the representation including atoms corresponding to a portion of at least one layer and including a portion of the interlayer space; and
    arranging a plurality of the unit cells into a supercell representation of the clay mineral.

3. The method of claim 1, wherein the clay structure of the representation corresponds to kaolinite.

4. The method of claim 1, wherein the clay structure of the representation corresponds to a clay selected from the group consisting of montmorillonite and pyrophyllite.

5. The method of claim 1, wherein the plurality of water molecules are arranged as one, two, or three layers of water molecules disposed in the interlayer space.

6. The method of claim 1, wherein the selected substitution sites are represented by magnesium ions replacing aluminum atoms in an octahedral sheet.

7. The method of claim 6, wherein the counterion species comprises sodium ions.

8. The method of claim 6, wherein the counterion species comprises calcium ions.

9. The method of claim 1, wherein operating the computer system to perform a molecular dynamics simulation comprises:
    calculating movement of counterions in the molecular representation at a plurality of sample times during the simulation time interval; and
    storing, in memory of the computer system, positions of the counterions during the simulation time interval;
    and wherein calculating self-diffusion coefficients comprises:
        retrieving, from memory of the computer system, stored positions of counterions corresponding to at least a subset of the plurality of sample times during the simulation time interval;
        calculating an average displacement of the counterions based on the retrieved positions; and
        calculating a self-diffusion coefficient for a counterion species from the average displacement.

10. The method of claim 9, further comprising orthogonalizing the molecular representation prior to operating the computer system to perform the molecular dynamics simulation.

11. The method of claim 1, wherein calculating ion conductivity for a species of counterions from its self-diffusion coefficient comprises applying the calculated self-diffusion coefficient to the Nernst-Einstein relationship to determine the ion conductivity of the species.

12. A method of analyzing a rock sample comprising a clay component implemented by a computer system, comprising:
    estimating the conductivity of the clay component in the rock sample;
    segmenting a digital image volume corresponding to one or more tomographic images of the rock sample, to associate voxels in the digital image volume with pore space, solid material, or the clay component; and
    assigning a relative conductivity value to voxels corresponding to the clay component relative to the conductivity of a fluid occupying the pore space of the sample;
    determining at least one petrophysical property of the rock sample based on an analysis of a representation of the digital image volume; and
    assessing a hydrocarbon reservoir in earth based on the at least one petrophysical property of the rock sample.

13. The method of claim 12, wherein estimating the conductivity of the clay component comprises:

constructing a molecular representation of the clay component, comprising:
   an anhydrous structure of atoms arranged in a plurality of parallel layers, the anhydrous structure including substitution sites in place of metal atoms in the structure at a concentration corresponding to a selected charge density;
   counterions of at least one species disposed in an interlayer space between layers of the anhydrous structure, at a concentration corresponding to the selected charge density; and
   a plurality of water molecules disposed in the interlayer space;
assigning force field parameters to the molecular representation in combination with boundary conditions corresponding to a selected pressure and temperature condition of the clay component;
operating the computer system to perform a molecular dynamics simulation of the equations of motion over a simulation time interval, to determine positional coordinates of counterions in the representation at a plurality of times during the simulation time interval;
calculating self-diffusion coefficients for one or more of the species of counterions from the positional coordinates at the plurality of times; and
calculating ion conductivities for a species of counterions from the self-diffusion coefficients.

14. The method of claim 13, wherein constructing the molecular representation comprises:
defining a unit cell of the representation including atoms corresponding to a portion of at least one layer and including a portion of the interlayer space; and
arranging a plurality of the unit cells into a supercell representation of the clay component.

15. The method of claim 12, further comprising acquiring the digital image volume of the rock sample, utilizing one of X-ray tomography, micro X-ray tomography, nano X-ray tomography, focused ion beam scanning electron microscopy, nuclear magnetic resonance, or neutron tomography.

16. The method of claim 15, wherein the rock sample comprises one of a whole core, side wall cores, outcrops, drill cuttings, laboratory generated synthetic rock samples, sand packs, and cemented packs.

17. A method of operating a computer system to calculate a formation factor for a rock system comprising a clay mineral, comprising:
constructing a model representation of a molecular fluid system, comprising:
   a plurality of unit cells of the molecular fluid populating a selected volume; and
   interstitial ions located disposed in the volume at a concentration corresponding to a selected charge density;
assigning force field parameters to the model representation;
operating the computer system to perform a molecular dynamics simulation of the equations of motion over a selected time duration, to determine positional coordinates of a plurality of species in the model representation at a plurality of times in the time duration;
calculating self-diffusion coefficients for one or more of the species from the positional coordinates at the plurality of times;
calculating bulk conductivity of the molecular fluid system from the self-diffusion coefficients;
determining an ion conductivity for the clay mineral;
calculating the formation factor as a ratio of the bulk conductivity of the molecular fluid system to the ion conductivity for the clay mineral;
determining at least one petrophysical property of the rock system based on the formation factor; and
assessing a hydrocarbon reservoir in earth based on the at least one petrophysical property of the rock system.

18. The method of claim 17, wherein determining an ion conductivity for the clay mineral comprises:
constructing a molecular representation of the clay mineral, comprising:
   an anhydrous structure of atoms arranged in a plurality of parallel layers, the anhydrous structure including substitution sites in place of metal atoms in the structure at a concentration corresponding to a selected charge density;
   counterions of at least one species disposed in an interlayer space between layers of the anhydrous structure, at a concentration corresponding to the selected charge density; and
   a plurality of water molecules disposed in the interlayer space;
assigning force field parameters to the molecular representation in combination with boundary conditions corresponding to a selected pressure and temperature condition of the clay mineral;
operating the computer system to perform a molecular dynamics simulation of the equations of motion over a simulation time interval, to determine positional coordinates of counterions in the representation at a plurality of times during the simulation time interval;
calculating self-diffusion coefficients for one or more of the species of counterions from the positional coordinates at the plurality of times; and
calculating ion conductivities for a species of counterions from the self-diffusion coefficients.

19. A system for analyzing material samples, the system comprising:
an imaging system configured to produce a digital image volume representative of a material sample; and
a computer system coupled to the imaging device and comprising:
   one or more processors; and
   one or more memory devices, coupled to the one or more processors, storing program instructions that, when executed by the one or more processors, cause the one or more processors to analyze a rock sample comprising a clay component by performing a plurality of operations comprising:
     segmenting a digital image volume corresponding to one or more tomographic images of the rock sample, to associate voxels in the digital image volume with pore space, solid material, or the clay component having an estimated conductivity; and
     assigning a relative conductivity value to voxels corresponding to the clay component relative to the conductivity of a fluid occupying the pore space of the sample;
     determining at least one petrophysical property of the rock sample based on an analysis of a representation of the digital image volume; and
     assessing a hydrocarbon reservoir in earth based on the at least one petrophysical property of the rock sample.

20. The system of claim 19, wherein the plurality of operations further comprises the operation of estimating conductivity of the clay component by a plurality of operations comprising:
- constructing a molecular representation of the clay component, comprising:
  - an anhydrous structure of atoms arranged in a plurality of parallel layers, the anhydrous structure including substitution sites in place of metal atoms in the structure at a concentration corresponding to a selected charge density;
  - counterions of at least one species disposed in an interlayer space between layers of the anhydrous structure, at a concentration corresponding to the selected charge density; and
  - a plurality of water molecules disposed in the interlayer space;
- assigning force field parameters to the molecular representation in combination with boundary conditions corresponding to a selected pressure and temperature condition of the clay mineral;
- performing a molecular dynamics simulation of the equations of motion over a simulation time interval, to determine positional coordinates of counterions in the representation at a plurality of times during the simulation time interval;
- calculating self-diffusion coefficients for one or more of the species of counterions from the positional coordinates at the plurality of times; and
- calculating ion conductivities for a species of counterions from the self-diffusion coefficients.

21. A system for analyzing material samples, the system comprising:
- an imaging system configured to produce a digital image volume representative of a material sample; and
- a computer system coupled to the imaging device and comprising:
  - one or more processors; and
  - one or more memory devices, coupled to the one or more processors, storing program instructions that, when executed by the one or more processors, cause the one or more processors to calculate a formation factor for a rock system comprising a clay mineral by performing a plurality of operations comprising:
    - constructing a model representation of a molecular fluid system, comprising:
      - a plurality of unit cells of the molecular fluid populating a selected volume; and
      - interstitial ions located disposed in the volume at a concentration corresponding to a selected charge density;
    - assigning force field parameters to the model representation;
    - performing a molecular dynamics simulation of the equations of motion over a selected time duration, to determine positional coordinates of a plurality of species in the model representation at a plurality of times in the time duration;
    - calculating self-diffusion coefficients for one or more of the species from the positional coordinates at the plurality of times;
    - calculating bulk conductivity of the molecular fluid system from the self-diffusion coefficients;
    - determining an ion conductivity for the clay mineral;
    - calculating the formation factor as a ratio of the bulk conductivity of the molecular fluid system to the ion conductivity for the clay mineral;
    - determining at least one petrophysical property of the rock system based on the formation factor; and
    - assessing a hydrocarbon reservoir in earth based on the at least one petrophysical property of the rock system.

22. The system of claim 21, wherein the operation of determining an ion conductivity for the clay mineral comprises:
- constructing a molecular representation of the clay mineral, comprising:
  - an anhydrous structure of atoms arranged in a plurality of parallel layers, the anhydrous structure including substitution sites in place of metal atoms in the structure at a concentration corresponding to a selected charge density;
  - counterions of at least one species disposed in an interlayer space between layers of the anhydrous structure, at a concentration corresponding to the selected charge density; and
  - a plurality of water molecules disposed in the interlayer space;
- assigning force field parameters to the molecular representation in combination with boundary conditions corresponding to a selected pressure and temperature condition of the clay mineral;
- performing a molecular dynamics simulation of the equations of motion over a simulation time interval, to determine positional coordinates of counterions in the representation at a plurality of times during the simulation time interval;
- calculating self-diffusion coefficients for one or more of the species of counterions from the positional coordinates at the plurality of times; and
- calculating ion conductivities for a species of counterions from the self-diffusion coefficients.

* * * * *